(12) United States Patent
Chapman, Jr.

(10) Patent No.: US 10,168,090 B1
(45) Date of Patent: *Jan. 1, 2019

(54) TEMPERATURE CONTROLLED BOX SYSTEM

(71) Applicant: EFP LLC, Elkhart, IN (US)

(72) Inventor: Learmond A. Chapman, Jr., Smyrna, TN (US)

(73) Assignee: EFP LLC, Elkhart, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/249,622

(22) Filed: Aug. 29, 2016

Related U.S. Application Data

(63) Continuation-in-part of application No. 14/017,276, filed on Sep. 3, 2013, now Pat. No. 9,429,350, which is a continuation-in-part of application No. 13/843,334, filed on Mar. 15, 2013, now Pat. No. 9,366,469.

(60) Provisional application No. 61/687,945, filed on May 3, 2012.

(51) Int. Cl.
  *F25D 3/06* (2006.01)

(52) U.S. Cl.
  CPC ............ *F25D 3/06* (2013.01); *F25D 2201/10* (2013.01); *F25D 2303/082* (2013.01); *F25D 2303/0843* (2013.01); *F25D 2303/0844* (2013.01); *F25D 2303/0845* (2013.01)

(58) Field of Classification Search
  CPC ............... F25D 3/06; F25D 2303/0845; F25D 2201/10; F25D 2303/082; F25D 2303/0843; F25D 2303/0844; F25D 25/00
  See application file for complete search history.

(56) References Cited

U.S. PATENT DOCUMENTS

| | | | |
|---|---|---|---|
| 4,881,562 A * | 11/1989 | Wright | A61F 2/00 134/110 |
| 6,467,299 B1 * | 10/2002 | Coetzee | A61J 1/165 62/371 |
| 2014/0000306 A1 | 1/2014 | Chapman, Jr. | |
| 2014/0144161 A1 | 5/2014 | Pointer et al. | |

* cited by examiner

*Primary Examiner* — Ana Vazquez
(74) *Attorney, Agent, or Firm* — Shane V. Cortesi

(57) ABSTRACT

A box system for keeping medicine and other payloads at a desired temperature for prolonged periods of time is disclosed. The system generally includes three or more insulating materials between a refrigerant and the payload so that the payload is not cold-shocked by the refrigerant but instead maintains a desired temperature range during shipment. A box having foldable tabs for securing the materials to each other is also disclosed herein.

9 Claims, 20 Drawing Sheets

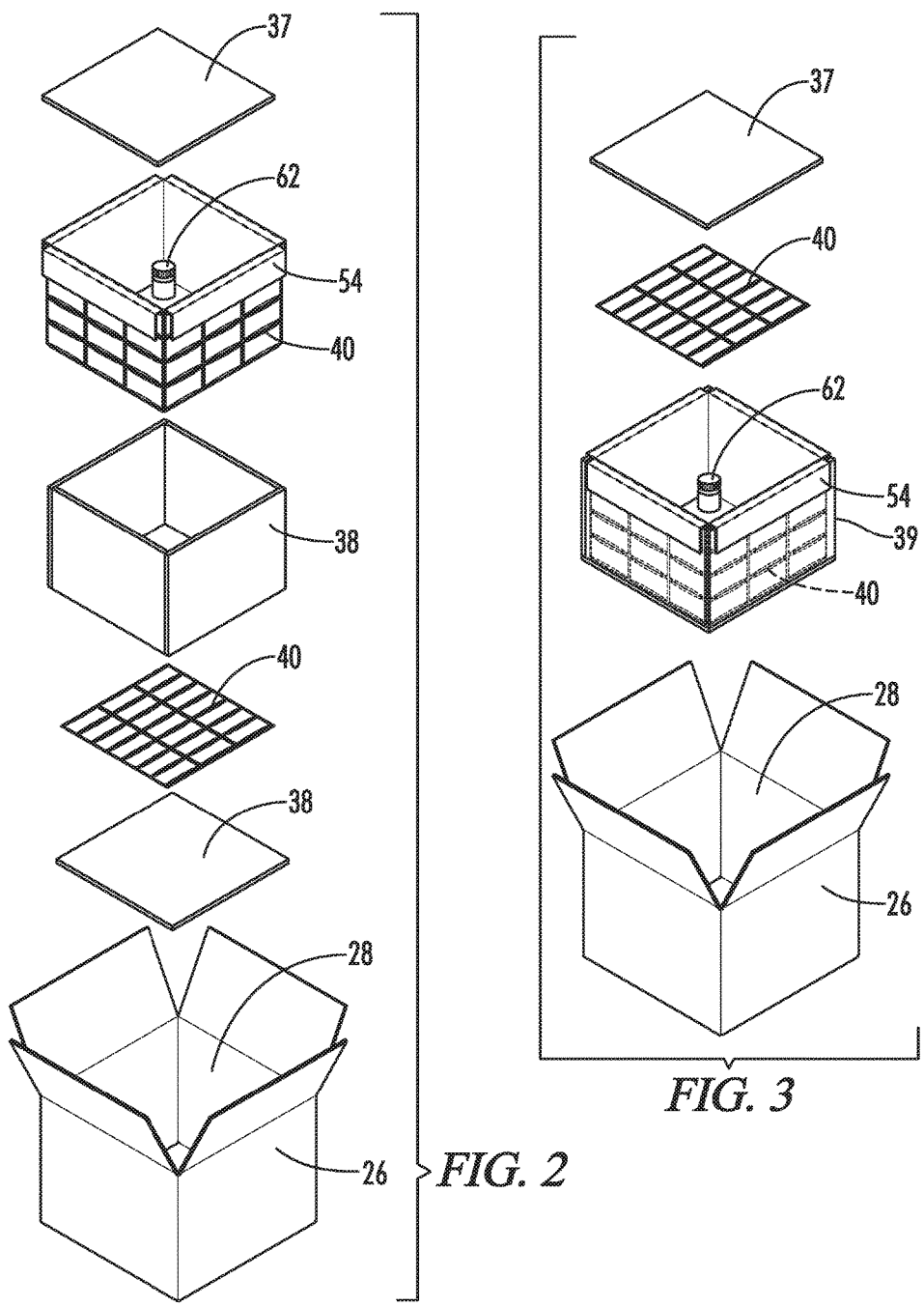

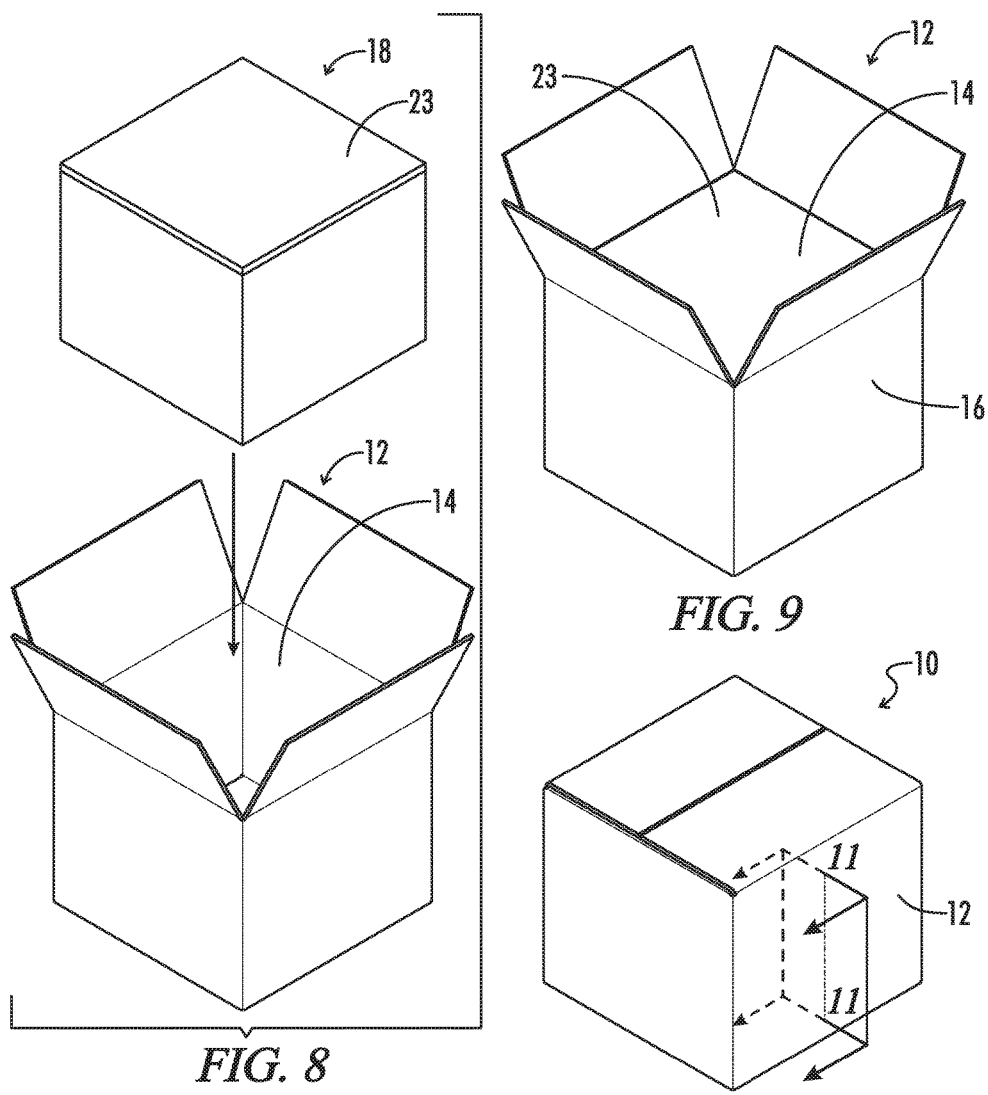

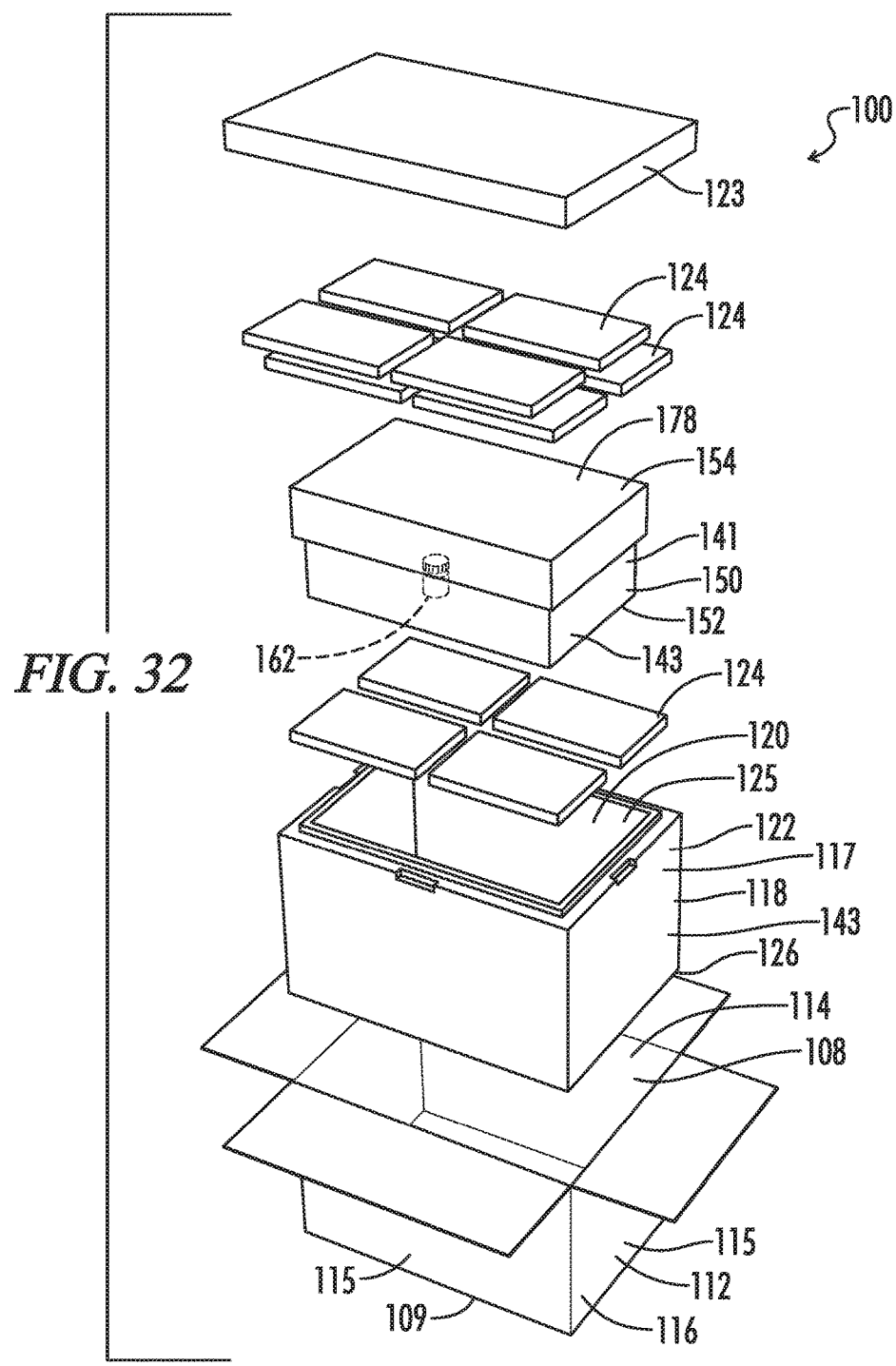

TEMPERATURE CONTROLLED BOX SYSTEM

CROSS-REFERENCES TO RELATED APPLICATIONS

This application is a continuation-in-part of U.S. patent application Ser. No. 14/017,276, filed Sep. 3, 2013 and entitled "BOX SYSTEM", which is a continuation-in-part of U.S. patent application Ser. No. 13/843,334 (now U.S. Pat. No. 9,366,469), entitled "Temperature Controlled Box System", filed Mar. 15, 2013, which claims the benefit of U.S. Provisional Application No. 61/687,945, entitled "Temperature Control for Shipping Containers Using Biased Ballast System", filed May 3, 2012, the contents of each of which are hereby incorporated by reference in their entirety.

TECHNICAL FIELD

The present invention relates to temperature-controlled boxes for shipping medicines and other payloads as well as to boxes having particular folding patterns.

BACKGROUND OF THE INVENTION

Many pharmaceutical manufacturers recommend that their medicines be kept at a temperature of between 2 degrees Celsius and 8 degrees Celsius at all times. Thus, various box systems have been developed to keep medicinal payloads at this temperature range during shipment.

Such prior art systems generally rely on an expensive phase change material to achieve the desired temperature range. For example, commonly, deuterium oxide (heavy water), which has a melting point of about 4 degrees Celsius, or decanol-1, which has a melting point of about 6.4 degrees Celsius, are used as phase change materials in shipping boxes to keep medicines at this temperature range during shipment. However, deuterium oxide and decanol-1 are very expensive.

U.S. Pat. No. 7,257,963 ("the '963 patent") teaches a system for shipping articles under controlled temperature conditions. As illustrated in FIGS. 3 and 4, the system includes an outside container 100 such as corrugated cardboard. A series of sytrofoam insulated panels 149 line the inside walls of the outside container 100. A plurality of chambers 250 containing ice/water are seated inside the insulated panels 149 and hold the interior temperature at 0 degrees Celsius for so long as it takes to melt and/or freeze the water/ice mixture. A second series of sytrofoam insulated panels 249 are positioned adjacent the interior walls of the chambers 250. Finally, a second phase change material 300, deuterium oxide, is placed inside the second series of insulated panels 249 to create a retention chamber. The payload is placed in the retention chamber. The system described in the '963 patent, however, suffers from at least one very important disadvantage: it is very expensive. According to the '963 patent, the system described therein requires $100 in deuterium oxide alone.

U.S. Pat. No. 7,849,708 ("the '708 patent") describes a shipping system that uses 0.5 pounds of decanol-1. However, decanol-1 is very expensive. In addition, the systems described in the '708 patent are only for local one-day delivery and are not designed to keep the payload at the desired temperature range beyond a one-day period.

Thus, there is need for shipping systems that are effective in creating a temperature-controlled environment for payloads such as medicines (e.g., pharmaceuticals and biologics) that keep such medicines at a desired range for a prolonged period of time and can be produced and sold at a fraction of the price of the systems currently on the market.

BRIEF SUMMARY

The present invention relates to a box system for keeping medicine and other payloads at a desired temperature for prolonged periods of time. In some embodiments, the system generally includes three or more insulating materials between a refrigerant and the payload so that the payload is not cold-shocked by the refrigerant and also does not suffer from heat-shock but instead maintains a relatively constant temperature range during shipment. An advantage of the box system of certain embodiments of the present disclosure is that the system allows a shipper to use a temperature controlled system that is effective in controlling temperature without the need for any expensive phase change materials.

In some embodiments, the box system includes a first outer box having an exterior and an interior, a refrigerant disposed in the first outer box interior; a container comprising an interior and an exterior, the container disposed interior to the refrigerant within the first outer box; a payload disposed in the container interior; a first insulating material disposed between the refrigerant and the container, a second insulating material disposed between the first insulating material and the container, and a third insulating material disposed between the second insulating material and the container, wherein the second insulating material is different from the first insulating material and the third insulating material. The first insulating material forms a first barrier between the refrigerant and the container. The second insulating material forms a second barrier between the refrigerant and the container, is disposed between the first barrier and the container and optionally substantially lines the first barrier. The third insulating material forms a third barrier between the refrigerant and the container, is disposed between the second barrier and the container and optionally substantially lines the first barrier. Optionally, the box system further includes a fourth insulating material disposed between the third insulating material and the container.

Optionally, the refrigerant is a water-based refrigerant, such as ice, the payload is a medicine having a temperature between about 2 degrees and about 8 degrees Celsius. Preferably, the box system is configured to maintain the medicine at a temperature of between about 2 degrees and about 8 degrees Celsius for at least about 72 hours, more preferably at least about 120 hours under conditions at least as stringent as ISTA 7D Summer (2007), ISTA 7D Winter (2007), ISTA 7E Summer (2010) and/or ISTA 7E Winter (2007). In some embodiments, the box system is configured to maintain the medicine at a temperature of between about 2 degrees and about 8 degrees Celsius for up to about 144 hours. Optionally, the first, second third, and fourth (if included) insulating material each are an insulant selected from the group consisting of liquid water, corrugated cardboard, polyurethane, polyethylene, expanded polyethylene, expanded polypropylene, polypropylene, expanded polystyrene, extruded polystyrene, and corrugated plastic. In addition, one or more of the insulants may be petroleum jelly.

Preferably, the first outer box interior contains no more than about 0.25 pounds (i.e., 0 to about 0.25 pounds, more preferably 0 to about 0.1 pounds) of a phase change material having a melting point between about 2 degrees Celsius and about 8 degrees Celsius. Optionally, the first outer box interior does not have an electrically-powered temperature control device and the box system is configured to retain the desired temperature range without electricity. Optionally, the box system further includes a second outer box, and the second outer box has an interior and an exterior, and the first outer box is located in the second outer box interior. Optionally, the first outer box is made of expanded polystyrene. Optionally, the box system has substantially no refrigerant adjacent to the payload container.

The present disclosure also provides an inner box for use in the box system and the inner box may form the third barrier. The inner box is generally rectangular in shape and has an open top, a bottom, and four sides, each of which has a top, a bottom, and a height extending from the top of the side to the bottom of the side, and the tops of the sides each have a generally rectangular tab extending therefrom. The tabs may have a first foldline, located at the intersection of the top sides and the tabs, along which the tabs are configured to fold horizontally relative to the tops, and the tabs include a second foldline along which the tabs are configured to fold vertically relative to the tops. Optionally, the tabs are configured such that when the tabs are folded horizontally along the first foldline and vertically along the second foldline, the tabs do not extend to the bottoms of the sides.

In some embodiments, the box system relies on an insulating container box comprised of cardboard. More particularly, in some embodiments, the box system includes: a) a first outer box having an exterior, an interior, a bottom, a plurality of sides extending upwardly from the bottom, and a lid; b) an insulating container comprising an interior, an exterior, a bottom, a plurality of sides extending upwardly from the insulating container bottom, and a lid, at least one of the insulating container bottom, the insulating container sides and the insulating container top comprising an outer layer comprising cardboard, a first middle layer interior to said outer layer and comprising an insulating material other than cardboard, and an inner layer comprising cardboard interior to said outer layer and said first middle layer, c) a payload disposed in said insulating container interior; and d) a refrigerant disposed in said first outer box interior and exterior to said insulating container, at least a portion of said refrigerant located between said first outer box and said outer layer. In some embodiments, the outer layer, the first middle layer and the inner layer are located at the bottom of the insulating container, and at least a portion of the refrigerant is disposed below the insulating container bottom and above the first outer box bottom, which provides at least three insulating materials between the bottom refrigerant and the payload. In some embodiments, the insulating container bottom has a length and a width and the first middle layer is centered on the container bottom and does not extend more than about 75% of the length and more than about 75% of the width of the insulating container bottom. In some embodiments, at least a portion of the refrigerant is disposed above the insulating container lid and below the first outer box lid. In some embodiments, the refrigerant has a temperature of less than about 25° C. (more preferably no more than about 0° C.). In some embodiments, the refrigerant comprises a water-based refrigerant such as ice, gel bricks and/or gel packs. In some embodiments, the box system is configured to maintain the payload at a temperature of between about 2 degrees and about 8 degrees Celsius for at least about 72 hours, more preferably at least about 96 hours and even more preferably at least about 120 hours, under conditions at least as stringent as ISTA 7D Winter (2007), ISTA 7D Summer (2007), ISTA 7E Winter (2010) and/or ISTA 7E Summer (2010). In some embodiments, the box system further comprises a second middle layer comprising a second insulating material, the second insulating material not cardboard and different than said first insulating material, the second middle layer located between the outer layer and the first middle layer. In some embodiments, the box system further comprises a middle cardboard layer between the first and the second middle layers. In some embodiments, at least one of the sides comprises an outer side layer comprising cardboard, a middle side layer interior to said first side layer and comprising an insulating material other than cardboard, and an inner side layer comprising cardboard interior to said outer and middle side layers. In some embodiments, all sides and the bottom of the insulating container comprise an outer layer comprising cardboard, a first middle layer interior to said outer layer and comprising an insulating material other than cardboard, and an inner layer comprising cardboard interior to said outer layer and said first middle layer. In some embodiments, the lid comprises a top lid layer comprising cardboard, a middle lid layer below said top lid layer and comprising an insulating material other than cardboard, and a bottom lid layer comprising cardboard below said top and middle lid layers. In some embodiments, the insulating material is an insulant selected from the group consisting of liquid water, polyurethane, polyethylene, expanded polyethylene, expanded polypropylene, polypropylene, expanded polystyrene, extruded polystyrene, and corrugated plastic. In addition, one or more of the insulants may be petroleum jelly. In some embodiments, the insulating material is liquid water and the payload has a temperature of between about 2 degrees Celsius and 8 degrees Celsius. In some embodiments, the insulating material is at room temperature (e.g. about 22 degrees Celsius) and the payload has a temperature of between about 2 degrees Celsius and about 8 degrees Celsius. In some embodiments, the first outer box contains no more than about 0.25 pounds of a phase change material having a melting point between about 2 degrees Celsius and about 8 degrees Celsius. In some embodiments, the payload is a medicine having a temperature between about 2 degrees and about 8 degrees Celsius. In some embodiments, the insulating container is generally rectangular in shape with a front side, a rear side and a left side and a right side. In some embodiments, the insulating container has a volume of at least about 0.1 cubic feet, more preferably at least about 0.5 cubic feet. In some embodiments, the insulating container interior has substantially no refrigerant. In some embodiments, the box system further comprises a second outer box, the second outer box having an interior and an exterior, and the first outer box is located in the second outer box interior. In some embodiments, the first outer box is comprised of expanded polystyrene. In some embodiments, the first outer box interior does not have an electrically-powered temperature control device.

In some embodiments, the insulating box is generally rectangular in shape and comprises an open top, a bottom, and four sides (i.e., a front, a rear, a left side and a right side), each side having a top, a bottom, and a height extending from the top of the side to the bottom of the side, and the top of at least one side (and preferably at least two opposite sides) has a tab extending therefrom, the tab having a first foldline, located at the intersection of the tab and the top of the least one side, in which the tab is configured to fold horizontally relative to the top, a second foldline in which the tab is configured to fold vertically relative to the top and a third foldline in which the tab is configured to fold horizontally across at least a portion of the bottom of the box. In some embodiment, the tab secures a first insulating material to said box. In some embodiments, the tab and the sides are comprised of a continuous piece of cardboard. In some embodiment, the top of two opposite sides (i.e., the left and right sides or the front and rear sides) each comprise a tab extending therefrom, the tabs having a first foldline, located at the intersection of the tabs and the tops of the opposite sides, in which the tabs are configured to fold horizontally relative to the tops, a second foldline in which the tabs are configured to fold vertically relative to the tops and a third foldline in which the tabs are configured to fold horizontally across at least a portion of the bottom of the box. In some embodiments, when the tabs fold on the third foldline across at least a portion of the bottom of the box, one tab is located above the other tab. In some embodiments, the tabs are folded on the third foldline across at least a portion of the bottom of said box, one tab is located above the other tab and a first insulating material is located between the tabs at the bottom of the box. In some embodiments, the box further includes a lid generally rectangular in shape that has a top, and four sides, each side having a top, a bottom, and a height extending from the top of the side to the bottom of the side, and the bottom of at least one lid side comprises a lid tab extending therefrom, the lid tab having a first foldline, located at the intersection of the lid tab and the bottom of the least one side of said lid, in which said tab is configured to fold horizontally relative to said bottom of the side of said lid, a second foldline in which said tab lid is configured to fold vertically relative to said bottom of the side of said lid and a third foldline in which the tab is configured to fold horizontally across at least a portion of the top of the lid. In some embodiments, the lid tab is folded on the third foldline to form at least a portion of the bottom of the lid and an insulating material is located above the tab.

Preferably, the box systems are configured to protect the payload from cold shock as well as heat shock.

BRIEF DESCRIPTION OF THE DRAWINGS

FIG. 2 illustrates an isometric, exploded view of first, second, third and fourth insulating materials for use in a box system of one embodiment of the present invention; the first and fourth insulating materials are corrugated cardboard, the second insulating material is expanded polystyrene and the third insulating material is a water jacket.

FIG. 3 illustrates an isometric, exploded view of first, second, third and fourth insulating materials for use in a box system of one embodiment of the present invention; the first and fourth insulating materials are corrugated cardboard, the second insulating material is expanded polystyrene and the third insulating material is a water jacket.

FIG. 8 illustrates an isometric, exploded view of a first outer box being placed in a second outer box.

FIG. 9 illustrates an isometric view of a second outer box; the top of the second outer box is open.

FIG. 10 illustrates an isometric view of the second outer box of FIG. 9 with its top closed.

in FIG. 27, the front tab is folded downwards along its second foldline.

in FIG. 28, the front and rear tabs are folded downwards along their second foldlines.

in FIG. 29, the left, front and rear tabs are folded downwards along their second foldlines.

in FIG. 30, the left, right, front and rear tabs are folded downwards along their second foldlines.

FIG. 32 is a side, perspective exploded view showing the packout of EXAMPLE 4.

DETAILED DESCRIPTION

Figure 1:
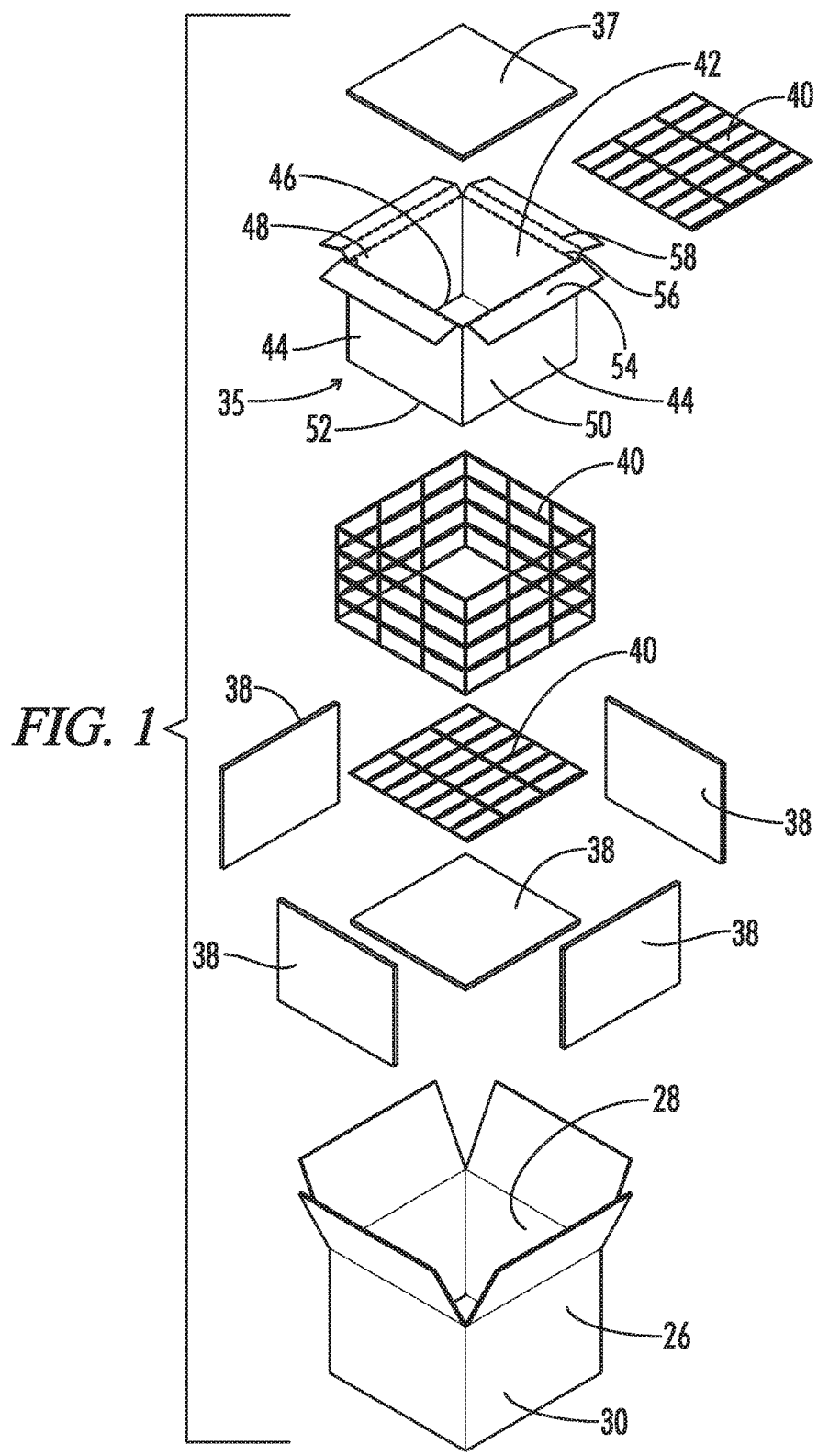
FIG. 1 illustrates an isometric, exploded view of first, second, third and fourth insulating materials for use in a box system of one embodiment of the present invention; the first and fourth insulating materials are corrugated cardboard, the second insulating material is expanded polystyrene and the third insulating material is a water jacket.

The present invention relates to a box system for keeping medicine and other payloads at a desired temperature for prolonged periods of time. In some embodiments, the system generally includes three or more insulating materials between a refrigerant and the payload so that the payload is not cold-shocked by the refrigerant but, instead, maintains a desired temperature range during shipment. An advantage of the box system of certain embodiments of the present disclosure is that the system allows a shipper to use a temperature controlled system that is effective in controlling temperature without the need for any expensive phase change materials. Without being bound to any particular theory, it is believed that creating a system in which several different types of insulating materials are located between the refrigerant and the payload delays the transfer of thermal energy between the refrigerant and the payload, and, thus allows for temperature, controlled conditions without the use of expensive phase change materials. It is believed that the first, second, and third insulating materials achieve a ballasting effect.

Referring now to the drawings, FIGS. 1-15 illustrate a temperature controlled box system generally designated by the numeral 10. In the drawings, not all reference numbers are included in each drawing for the sake of clarity.

Referring further to FIGS. 1-15, the box system 10 includes a first outer box 18 having an exterior 22 and an interior 20. One or more refrigerants 24, preferably several refrigerants, are disposed in the first outer box interior 20. In some embodiments, the refrigerants 24 are a plurality of frozen and/or refrigerated water-based gel packs. In some embodiments, the first outer box 18 is comprised of expanded polystyrene and the walls of the outer box 18 are about 1-2 inches in thickness. Preferably, the first outer box 12 has a lid 23, as shown in FIGS. 8-9. In some embodiments, the system 10 further includes a second outer box 12 that has an interior 14 and an exterior 16 and the first outer box 18 is disposed in the second outer box interior 14, as shown in FIGS. 8-11. In some embodiments, the second outer box 12 is comprised of corrugated cardboard.

The box system 10 further includes a payload 62 that is disposed interior to the refrigerant 24. The payload 62 may be any item that is desired to be kept within a certain temperature range. In some embodiments, the payload 62 is a medicine, food or an electronic device. The payload 62 may be in any form, including without limitation, solid or liquid form. Optionally, the payload 62 is disposed within a container 60. If the payload 62 is an electronic device, one or more of the components adjacent to the payload container 60, such as the lid 37 described below, may have anti-static properties. Preferably, the payload 62 is a medicine and the container 60 is a plastic pill bottle or a syringe.

A first insulating material 26 is disposed between the refrigerant 24 and the payload 62 and forms a first barrier between the refrigerant 24 and the payload 62. In some embodiments, the first insulating material 26 is provided in the form of a four-sided corrugated cardboard box, as shown in FIGS. 1-7, has an exterior 30, an interior 28, four sides 29, a closed bottom 32 and a top closeable by tabs 36. In addition to corrugated cardboard, the first insulating material 26 may be, for example, liquid water, polyurethane, polyethylene, expanded polyethylene, expanded polypropylene, polypropylene, expanded polystyrene, extruded polystyrene, and corrugated plastic. As used herein, "liquid water" means $H_2O$ and does not include deuterium oxide. In addition, the first insulating-material 26 may be petroleum jelly (more particularly containers comprising petroleum jelly), as preliminary tests have shown that a box system using a petroleum jelly insulating layer and two other insulant layers (such as those mentioned in the immediately preceding sentence), performs well in maintaining a temperature-controlled shipping system.

A second insulating material 38 is disposed between the first insulating material 26 and the payload 62 and forms a second barrier between the between the refrigerant 24 and the payload 62. Optionally, the second insulating material 38 substantially lines the first barrier, as best seen in FIG. 2, which shows the second insulating material 38 being loaded into the first insulating material 26. By substantially lining, it is meant that at least 75% of the surface area of a material is lined with another material. Usually, the second insulating material 38 is different than the first insulating material 26, because the difference of materials is believed to delay the transfer of thermal energy through the first and second insulating materials 26 and 38. In some embodiments, the second insulating material 38 is expanded polystyrene. In addition to expanded polystyrene, the second insulating material 38 may be, for example, corrugated cardboard, liquid water, polyurethane, polyethylene, expanded polyethylene, expanded polypropylene, polypropylene, extruded polystyrene, and corrugated plastic. In addition, the second insulating material 38 may be petroleum jelly.

A third insulating material 40 is disposed between the second insulating material 38 and the payload 62 and forms a third barrier between the between the refrigerant 24 and the payload 62. Optionally, the third insulating material 40 substantially lines the second barrier, as best seen in FIG. 3, which shows the third insulating material 40 surrounded by the second insulating material 38. Usually, the third insulating material 40 is different than the second insulating material 38, because, again, it is believed that the difference in materials delays the transfer of thermal energy through the second and third insulating materials 38 and 40. However, the third and first insulating materials 40 and 26 may be the same. In some embodiments, the third insulating material 40 is a water jacket (i.e., interconnected cells of liquid water), as shown in FIGS. 1-4. It has been observed that a water jacket having water at room temperature is a particularly good insulant for use with the present invention. If used, the water jacket is generally well above the freezing point of water (e.g., at least about 10 degrees Celsius and preferably about 22 degrees Celsius) so that the water jacket does not cold shock the payload 62. In addition to liquid water, the third insulating material 40 may be, for example, expanded polystyrene, corrugated cardboard, polyurethane, polyethylene, expanded polyethylene, expanded polypropylene, polypropylene, expanded polystyrene, extruded polystyrene, and corrugated plastic. In addition, the third insulating material 40 may be petroleum jelly.

Figure 4:
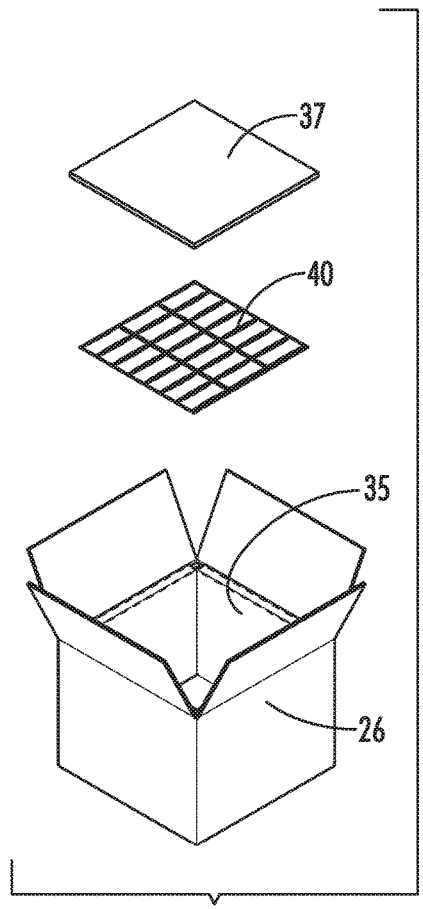
FIG. 4 illustrates an isometric exploded view of first and fourth insulating materials, which are corrugated cardboard; two lids, namely a water jacket and expanded polystyrene, are being placed on top of the fourth insulating material, specifically, on the ledges created by the tabs; second and third insulating materials, which are located between the first and fourth insulating materials, is not visible.
Figure 5:
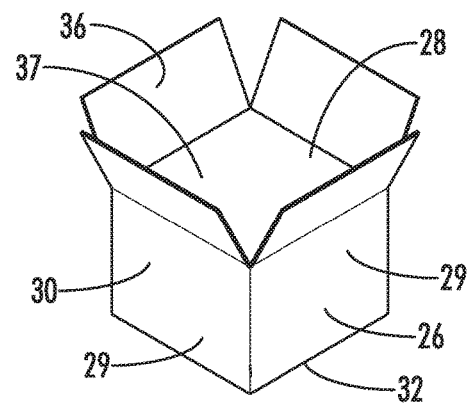
FIG. 5 illustrates an isometric view of a first insulating material, which is corrugated cardboard.
Figure 6:
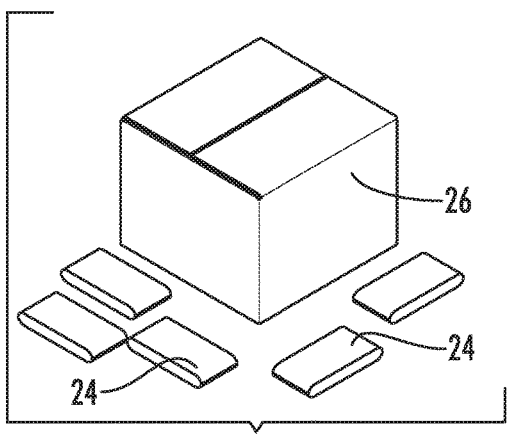
FIG. 6 illustrates an isometric view of a first insulating material, which is corrugated cardboard, and five refrigerant gels.
Figure 7:
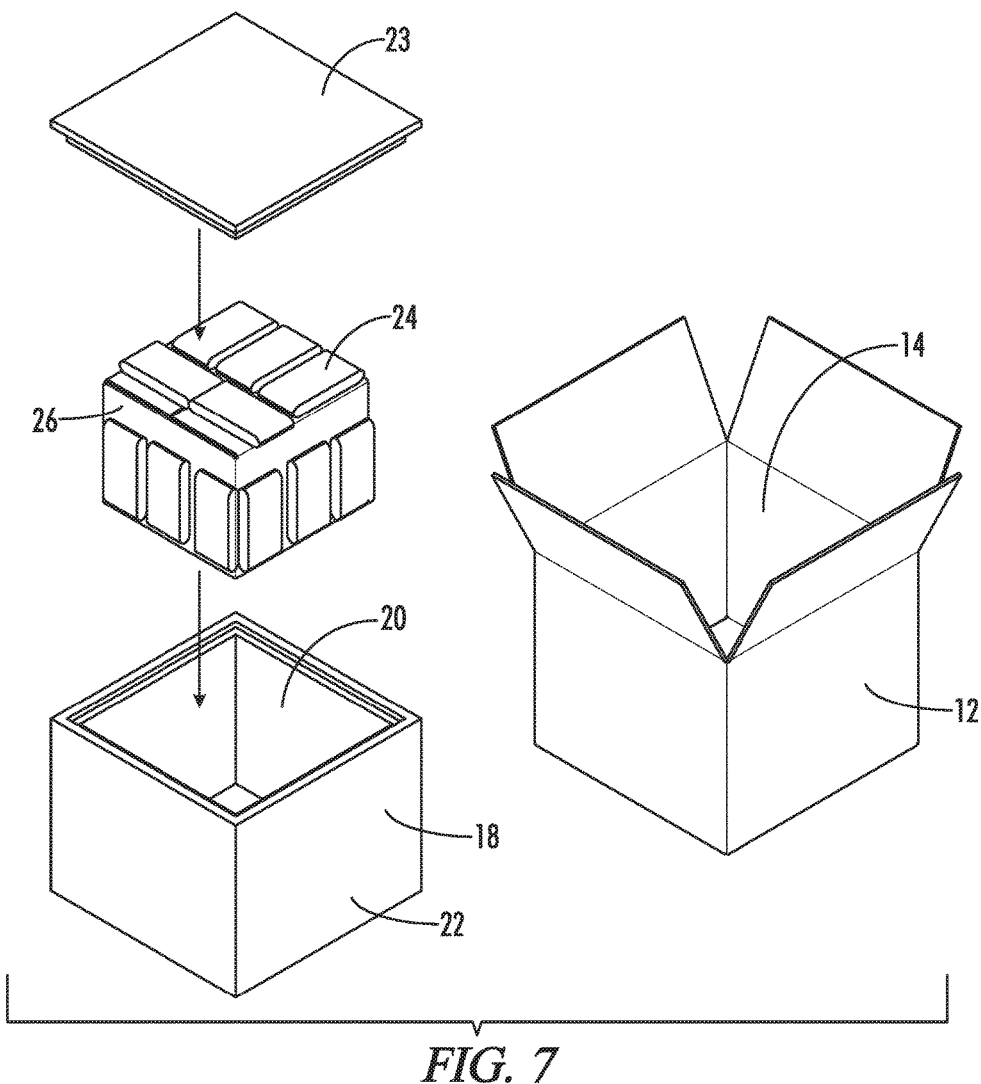
FIG. 7 illustrates an isometric, exploded view of a first insulating material, which is corrugated cardboard and is surrounded by refrigerant gels, being placed in a first outer box; a second outer box is located on the right side of FIG. 7.
Figure 11:
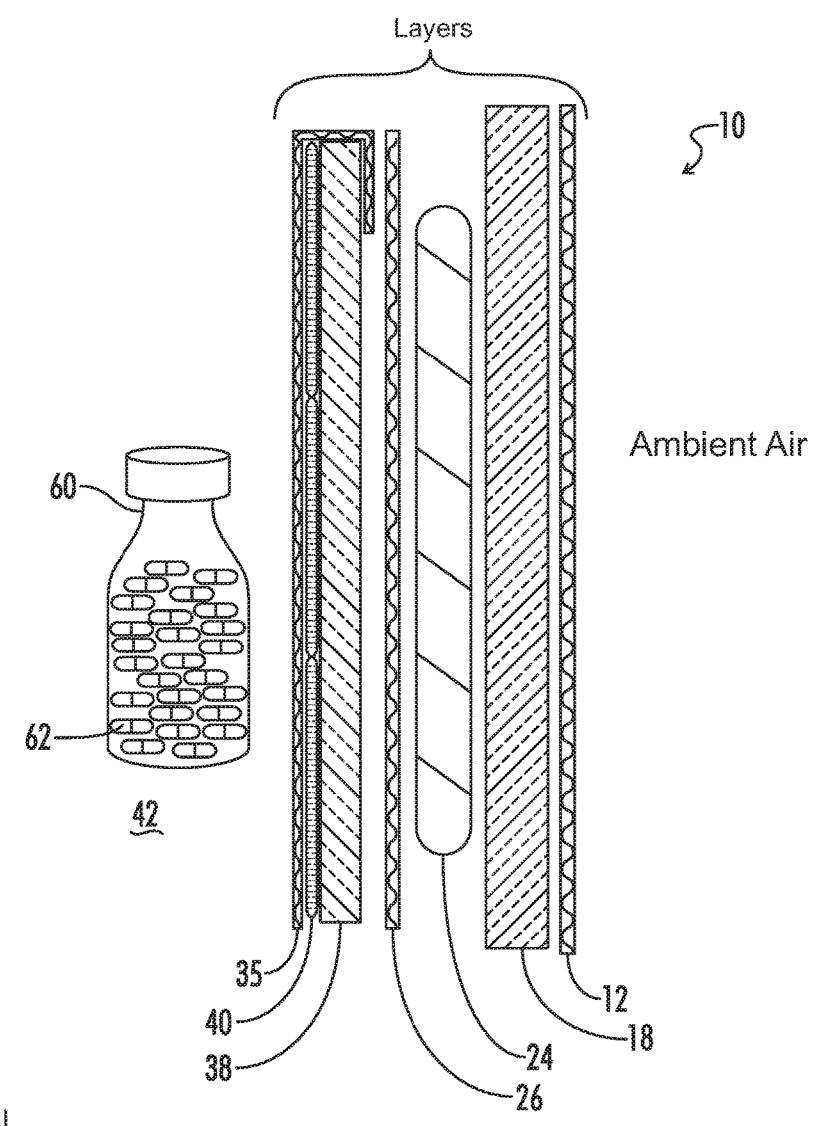
FIG. 11 is a representational diagram showing the insulating materials between the refrigerant and the payload container taken from plane 11-11 in FIG. 10.

Optionally, a fourth insulating material 35 is disposed between the third insulating material 40 and the payload 62 and forms a fourth barrier between the between the refrigerant 24 and the payload 62. Optionally, the fourth insulating material 35 substantially lines the third barrier, as best seen in FIG. 2, which shows the fourth insulating material 35 surrounded by the third insulating material 40. Usually, the fourth insulating material 35 is different than the third insulating material 40, because, again, it is believed that the difference in materials delays the transfer of passage of thermal energy through the third and fourth insulating materials 40 and 35. In some embodiments, the fourth insulating material 35 is provided in the form of an inner corrugated cardboard box, as shown in FIGS. 1-4, and has four sides 44, an interior 42, an exterior 50, a closed bottom 52 and an open top. The top may be closeable by an upper lid 37 comprised of an insulant. The system may include merely an upper lid 37, as shown in FIG. 2. Alternately, an insulant that is different from the insulant forming the upper lid 37 may be placed below the upper lid 37, as shown in FIGS. 3 and 4, where the third insulating material 40 is placed below the upper lid 37. Optionally, the four sides 44 each include a bottom 46, a top 48, a height extending from the top 48 of the side 44 to the bottom 46 of the side 44, and the tops 48 of the sides 44 each comprise a generally rectangular tab 54 extending therefrom. Optionally, the tabs 54 each have a first foldline/scoreline 56, located at the intersection of each tab 54 and top 48, along which the tabs 54 are configured to fold horizontally relative to said tops 48, and the tabs include a second foldline/scoreline 56 in which the tabs 54 are configured to fold vertically relative to said tops 48. Optionally, the tabs 54 are configured such that when the tabs 54 are folded horizontally along the first foldline 56 and vertically along the second foldline 58, the tabs 58 do not extend to the bottoms 46 of the sides 44. The tabs 54 generally do not provide additional insulation to the system 10 (because the tabs 54 are generally comprised of corrugated cardboard like the first layer 26 and in some embodiments do not extend to the bottoms 46 of the sides 44) but instead merely secure the insulating materials together, as best seen in FIGS. 2-3.

Optionally, the first outer box interior 14 does not have an electrically-powered temperature control device and the box system 10 is configured to retain the desired temperature range without electricity. Optionally, the box system 10 has substantially no refrigerant 24 adjacent to the payload container 60.

The illustrated Figures generally illustrate a single insulating layer that is comprised of a single material. For example, the innermost insulating layer is shown as a 4-sided cardboard box, the next innermost layer is a water-jacket that forms a 4-sided perimeter, the next innermost layer are four pieces of expanded polystyrene that form a 4-sided perimeter, and the next innermost layer is a 4-sided cardboard box. However, it will be appreciated that adjacent sides of any given layer may be comprised of different materials. However, generally at least three materials (i.e., the first, second, and third insulating materials 26, 38 and 40) are between most, if not all, refrigerants 24 and the payload container 62 and the second insulating material 38 is different than the first and third insulating materials 26 and 40. That said, it has been observed that the lid 37 is optional in some applications, such as where the payload container 60 is a syringe that, in itself, provides sufficient insulation. However, in such applications, there are usually three materials (i.e., the first, second, and third insulating materials 26, 38 and 40) forming a perimeter around the payload container 60 and the three materials provide an insulation between the side refrigerants 24 and the payload container 60. It has also been observed that in some cases, it is not desirable to place a room temperature water jacket adjacent to a container 60 that includes a low mass payload 62 (e.g., a syringe containing medicine), because the container 60 may transfer its thermal energy to the water jacket too quickly.

In some embodiments, one of the first, second, third, and fourth insulating materials 26, 38, 40 and 35 may be a coating that coats one of the other insulating materials.

In some embodiments, the first, second, third, and fourth insulating materials 26, 38, 40 and 35 are about 0.1 to about 1.0 inches thick.

In some embodiments, one of the first, second, third, and fourth insulating materials 26, 38, 40, and 35 may have a plurality of pores and the size of the pores may be different on opposite sides of the material so that thermal energy passes through the different sides at different speeds. For example, in one embodiment, the side facing the payload container 60 may have a first pore size and the side facing the refrigerant 24 may have a smaller pore size than the first pore size so that thermal energy enters the opposite sides at different rates.

The Embodiments of FIGS. 22-30 and 32

FIGS. 22-30 and 32 illustrate temperature controlled box systems 100 similar in function and design to the temperature controlled box system 10 of FIGS. 1-14 and 16-18. Referring further to FIGS. 22-30 and 32, the temperature controlled box system 100 includes a rectangular second outer box 112 that may be comprised of, for example, cardboard and has an interior 114, an exterior 116, four sides 115, a bottom 109, and a closeable top 108. The box system 100 further includes a first outer box 118 located in the second outer box interior 114 and the first outer box 118 includes an interior 120, an exterior 122, four sides 117, a bottom 126, and a lid 123 for closing the top 125 of the first outer box 118. Preferably, the first outer box 118 is comprised of an insulating material such as EPS. The first outer box interior 120 further includes a refrigerant 124 and an insulating container 141. The insulating container 141 has an interior 142, an exterior 150, four sides 143, a bottom 152 and a lid 154. A payload 162 is located in the insulating container interior 142. Refrigerant 124 is positioned between the walls of the first inner box 118 and the insulating container 141 (e.g., on the lid 154 of the insulating container 141, between the bottom 152 of the insulating container and the bottom 126 of the first inner box 118, and/or between the sides 143 of the insulating container 141 and the sides 117 of the first inner box 118).

Figure 22:
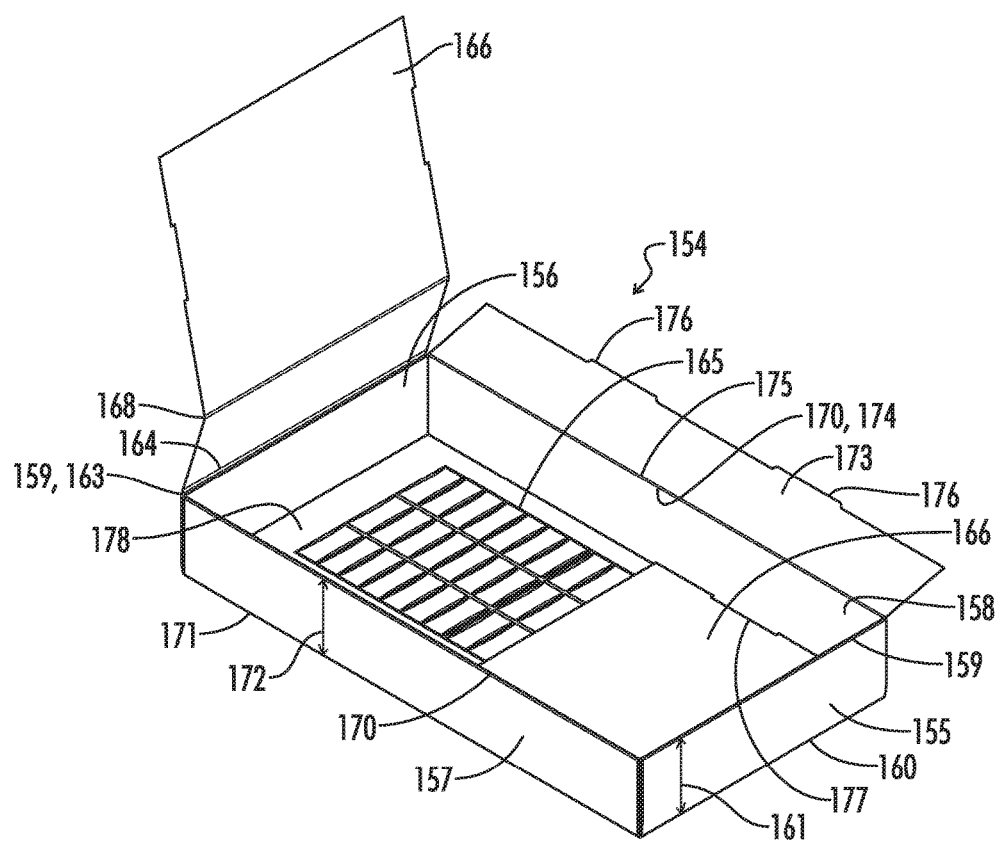
FIG. 22 is a bottom, perspective view of a box lid of another box system of the present invention; the rear tab, which forms part of the bottom panel of the lid, is folded upwards along its second foldline to show the presence of a water jacket below (in this view) the front and rear tabs; the right side tab is also folded to the right.
Figure 23:
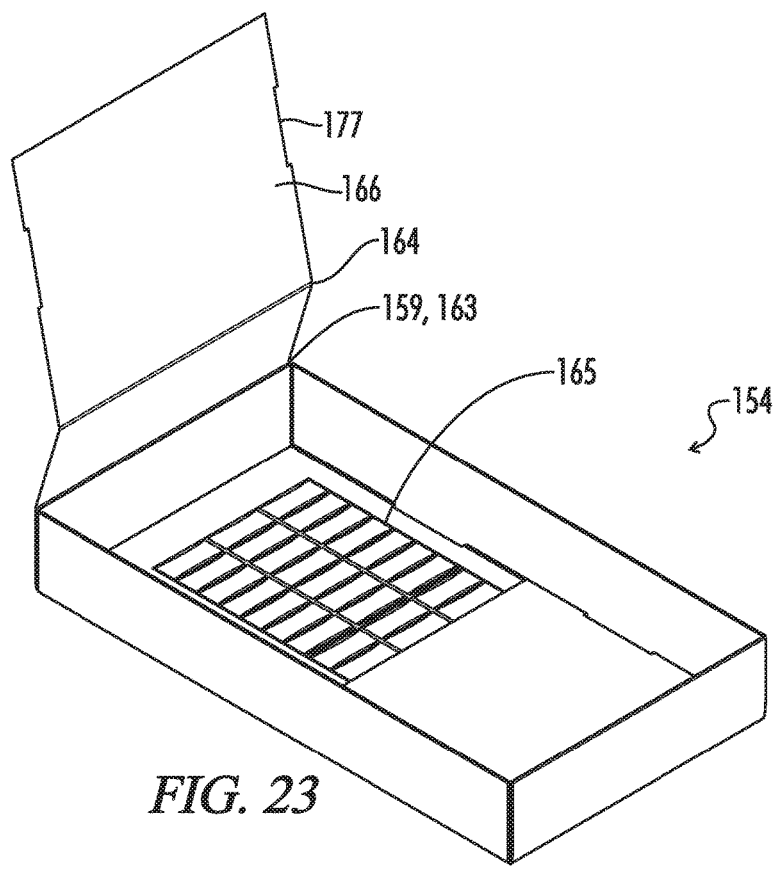
FIG. 23 is a bottom, perspective view of the box lid of FIG. 22 with the right side tab folded downwards along its second foldline.
Figure 24:
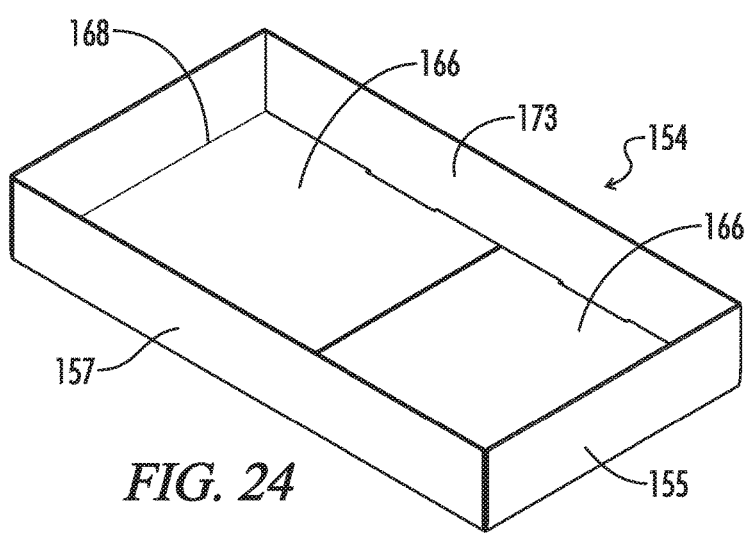
FIG. 24 is a bottom, perspective view of the box lid of FIG. 23 with the rear tab of the lid folded downwards along its second foldline.
Figure 25:
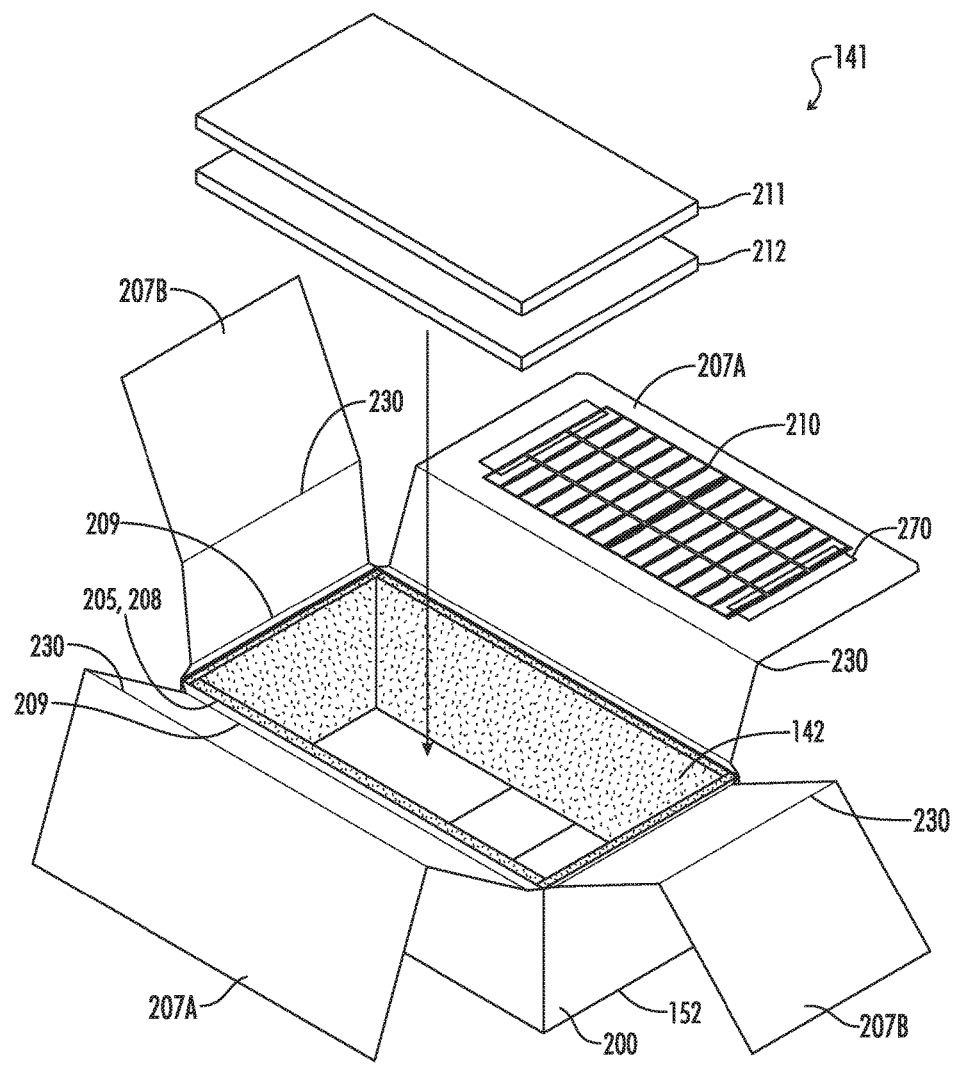
FIG. 25 is a top, exploded perspective view of an insulating container that is used in conjunction with the lid of FIG. 24.

The lid 154 of the insulating container 141 is shown in FIGS. 22-24 and the lid 154 has a front side 155, a rear side 156, a left side 157, and a right side 158, all of which are comprised of cardboard. The front and rear side 155 and 156 each have a bottom 159, a top 160, a height 161 extending from the bottom 159 to the top 160, and a tab 166 extending from the side bottoms 159. The front and rear tabs 166 have a first foldline/scoreline 163, located at the intersection of the bottom 159 of the side 155 and 156 and the tab 166, in which the tabs 166 are configured to fold horizontally relative to the bottom 159 of the sides 155 and 156, a second foldline/scoreline 164 in which the tabs 166 are configured to fold vertically relative to the bottom 159 of the sides 155 and 156, and a third foldline/scoreline 168 in which the tabs 166 are configured to fold horizontally relative to the bottom of the front and rear sides 155 and 156 to form a bottom panel of the lid 154. A water jacket 165 is located above the front and rear tabs 166, which creates three insulating materials between a refrigerant 124 located on top of the lid 154 and the payload 162, namely, the front and rear tabs 166 (which form an inner insulating layer), a middle insulating layer comprised of the water jacket 165, and the top 178 of the lid 154, which is comprised of cardboard. The left and right sides 157 and 158 further include a bottom 170, a top 171, and a height 172 extending from the top 171 to the bottom 170, and the left and right sides 157 and 158 include a tab 173 extending from the bottom 170 of the left side 157 and right side 158 and a first foldline/scoreline 174, located at the intersection of the tab 173 and the bottom 170 of the side 157 and 158, in which the side tab 173 is configured to fold horizontally relative to the bottom 170 of the side 157 and 158 and a second foldline/scoreline 175 in which the tab 173 is configured to fold vertically relative to the bottom 170 of the sides 157 and 158. Optionally, the side tabs 173 include a series of protrusions 176 that are configured to fit into recesses 177 in the front and rear tabs 166 to secure the lid 154 together.

Figure 26:
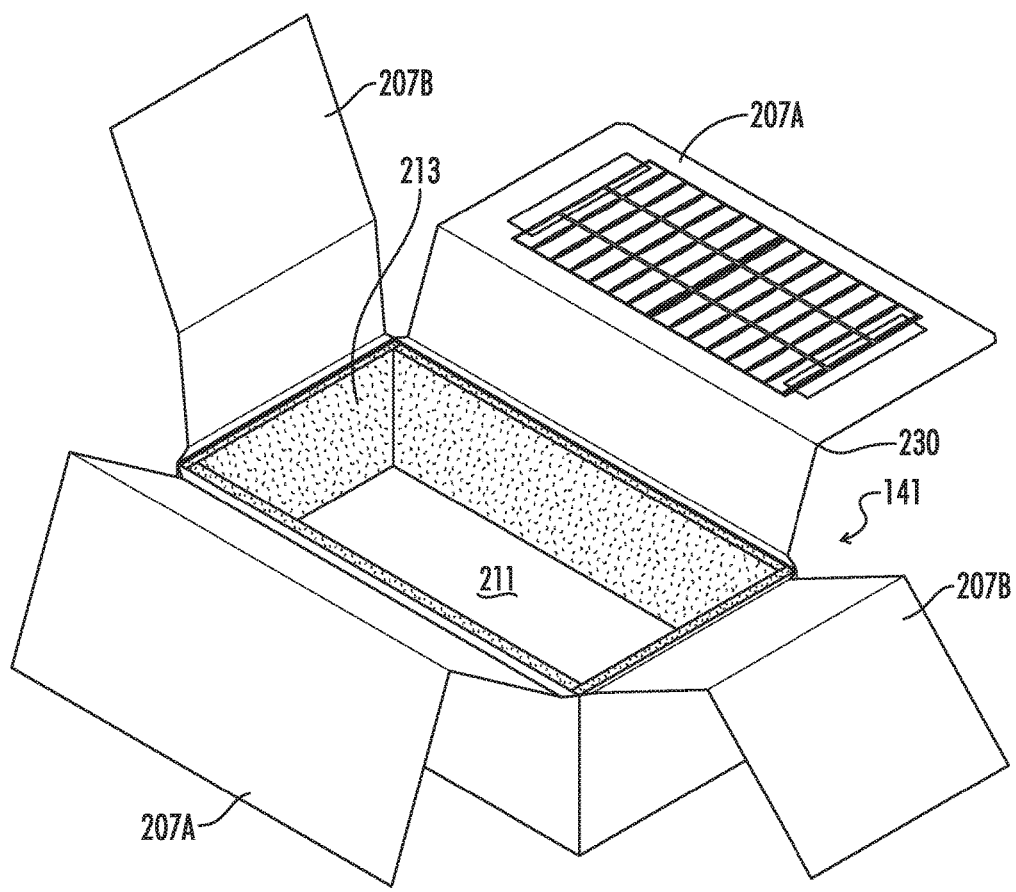
FIG. 26 is a top, perspective view of the insulating container of FIG. 25 with the insulating materials located inside the container, in FIG. 26, all tabs are folded upwards along their second foldlines.
Figure 27:
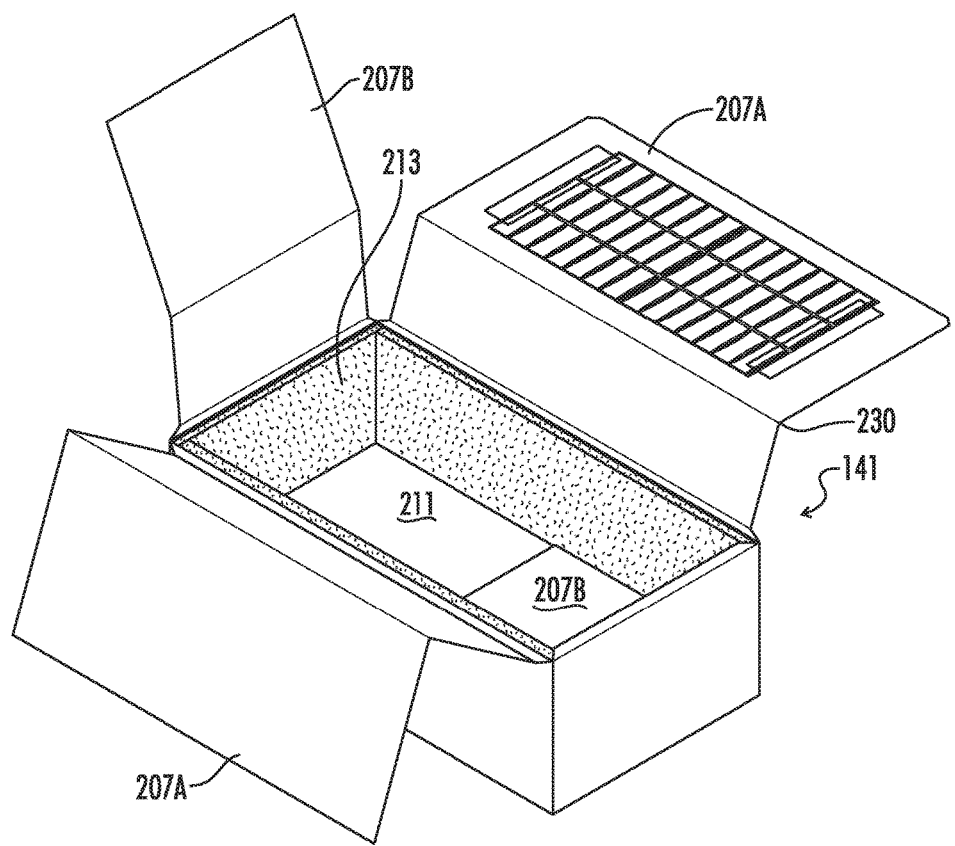
FIG. 27 is a top, perspective view of the insulating container of FIG. 26.
Figure 28:
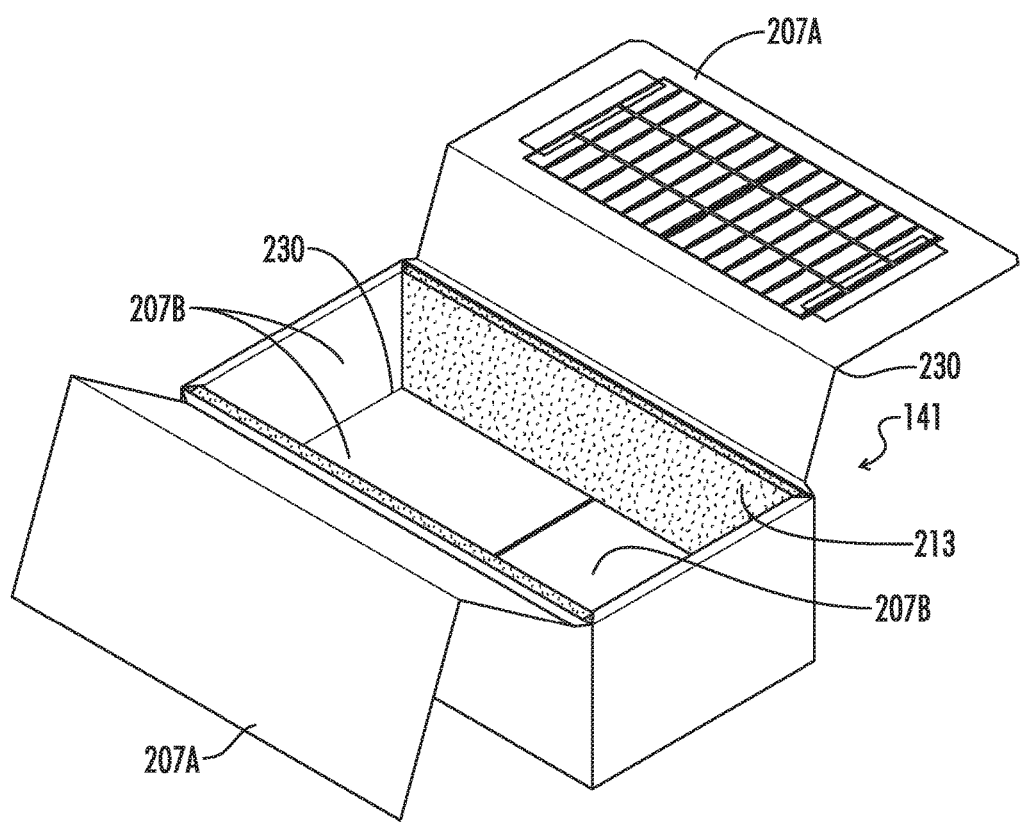
FIG. 28 is a top, perspective view of the insulating container of FIG. 27.
Figure 29:
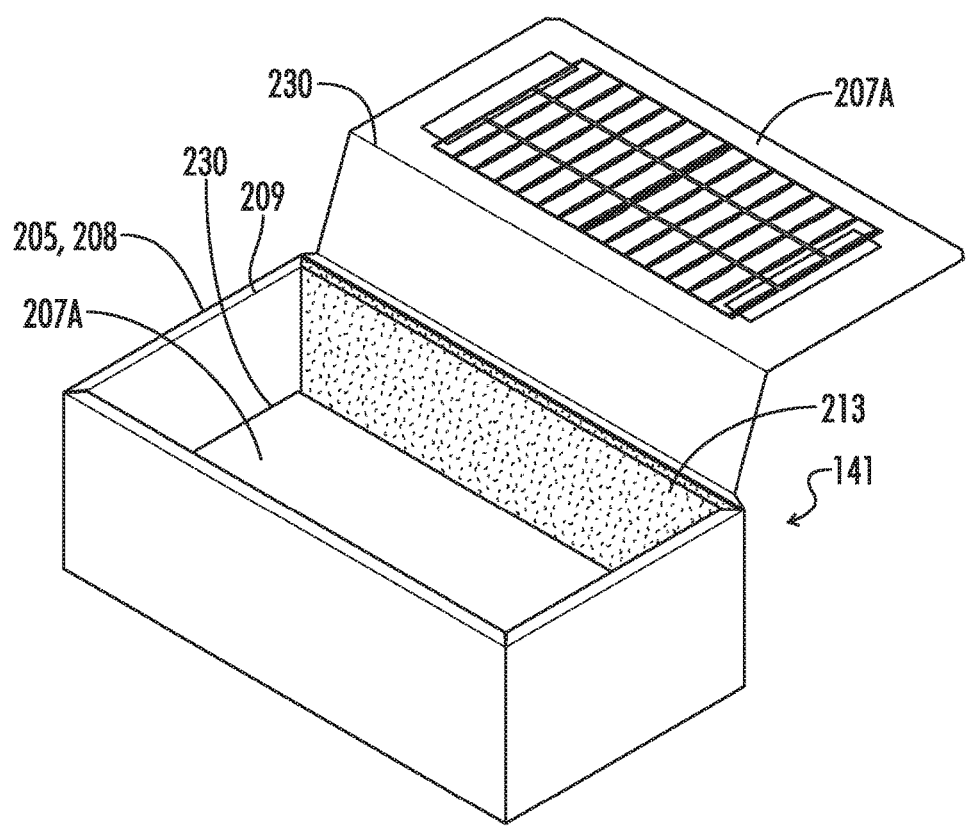
FIG. 29 is a top, perspective view of the insulating container of FIG. 28.
Figure 30:
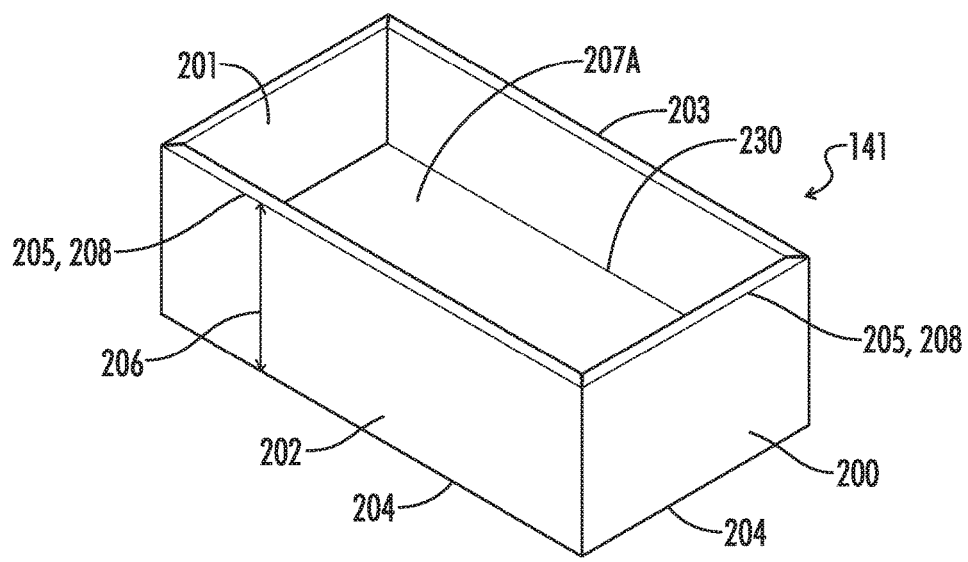
FIG. 30 is a top, perspective view of the insulating container of FIG. 29.

FIGS. 25-30 illustrate how the sides of the inner container 141 may include similar foldlines/scorelines. More particularly, as shown in FIGS. 25-30, the inner container 141 has a front side 200, a rear side 201, a left side 202, and a right side 203, all of which are comprised of cardboard (e.g., corrugated cardboard). The front, rear, left and right sides 200-203 each have a bottom 204, a top 205, a height 206 extending from the bottom 204 to the top 205, and a tab 207A or 207B extending from the side tops 205. (Tab 207B refers to the tabs attached to the front and rear sides, whereas tab 207A refers to the tabs attached to the right and left sides). The tabs 207A and 207B have a first foldline/scoreline 208, located at the intersection of the top 205 of the sides 200-203 and the tab 207A and 207B, in which the tabs 207A and 207B are configured to fold horizontally relative to the top 205 of the sides 200-203, a second foldline/scoreline 209 in which the tabs 207A and 207B are configured to fold vertically relative to the top 205 of the sides 200-203, and a third foldline/scoreline 230 in which the tabs 207A and 207B are configured to fold horizontally relative to the top 205 of the sides 200-203. Preferably, the inner container interior 142 includes three insulating materials 210, 211 and 212 and the insulating materials 210-212 are either stacked, or more preferably, spaced between the cardboard tabs 207A and 207B so that the insulated container 141 includes a series of insulants (namely insulating materials 210-212 and the tabs 207A and 207B) between the payload 162 and bottom refrigerant 124 (which is located between the bottom 152 of the insulating container 141 and the bottom 126 of the first outer container 118). Optionally, an insulating material 210 is a water jacket that is glued to a tab 207A or 207B or taped to the tab 207A or 207B with tape 270. Preferably, the cardboard tabs 207A and 207B are spaced between the insulating materials 210-212 (which preferably are not comprised of cardboard) so that the insulated container 141 includes a series of different insulants between the payload 162 and refrigerant 124 located between the bottom 152 of the insulating container 141 and the bottom 126 of the first outer container 118. Without being bound to any particular theory, it has been found that, at least in some embodiments, it is important to include more types of different insulants at the bottom 152 of the insulated container 141 as compared to the lid 154 and the sides 200-203. In some embodiments, as best seen in FIGS. 26-28, the sides 200-203 include an insulated material 213 other than cardboard and the insulated material 213 is sandwiched between tabs 207A and the outside of the insulated container 141. This side insulated material 213 may or may not be needed, depending on for example, the length of time the payload is desired to be kept in a particular temperature range, the variation that is allowed in the temperature range, whether refrigerant 124 is located adjacent to the sides 200-203 of the insulated container 141, and the temperature outside of the second outer box 112. It has been found that water jacket insulated material located in, for example, the lid 154 or bottom 152 of the insulated container 141 preferably covers only a portion surface area of the lid 154 or bottom 152 and preferably is centrally located relative to the width and length of the lid 154 or bottom 152, which may be attributable to the fact that the payload 162 in the widthwise and lengthwise center (e.g., the center pill bottle) is further insulated from heat outside of the second outer box 112 by payload 162 adjacent to the center payload 162 (e.g., surrounding pill bottles). It has been found that the folding design shown in FIGS. 22-30 and 32 is particularly well-suited for shipping due to the fact that only a few components need to be provided and the system 200 can be packaged with few steps. It has also been observed that the order of insulating materials can affect the performance of the system 200 but that optimal ordering of insulating materials can be readily ascertained through testing.

Terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

The following examples describe various embodiments of the present invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples.

Example 1

A temperature controlled shipping box system was prepared as follows. A rectangular ECT-32 (edge crush test) corrugated cardboard shipping box having a front, a rear, two sides, a closed bottom and a closeable top was provided. The shipping box had a length of 26 inches, a width of 17 inches and a height of 16.2 inches and was made of ECT-32⅜ inch thick corrugated cardboard. A rectangular EPS (expanded polystyrene) box having a front, a rear, two sides, a closed bottom, and a top closeable by a lid was placed inside the corrugated cardboard shipping box. The EPS box had a length of 23 inches, a width of 17 inches, a height of 13.2 inches and the expanded polystyrene forming the bottom, sides and lid was 1.5 inches thick and had 3 pcf (pounds per cubic feet) density. A first inner box (i.e., a first insulating material) was placed centrally inside the EPS box. The first inner box was made of 32 ECT ⅛ inch thick corrugated cardboard, had a front, a rear, two sides, a closed bottom, a closeable top, a length of 20.25 inches, a width of 13.5 inches, and a height of 9 inches. A first water jacket (i.e., a second insulating material) consisting of interconnected water cells and having a thickness of 0.5 inches was placed inside the first inner box and used to line the two sides and front and rear of the first inner box. A second water jacket consisting of interconnected water cells having a thickness of 0.5 inches was used to line the bottom of the first inner box. Five rectangular strips of 3 pcf expanded polystyrene (i.e., a third insulating material) having a thickness of 0.375 inches were placed interior to the first and second water jackets and used to line the water jackets. A second inner ECT-32 corrugated cardboard box (i.e., a fourth insulating material) having a front, a rear, two sides, a closed bottom, an open top, a thickness of 0.125 inches, a length of 18.75 inches, a width of 11.75 inches, and a height of 7.75 inches was placed interior to the expanded polystyrene strips and used to line the strips. The tops of the front, rear and two sides of the second inner corrugated cardboard box were scored to create four rectangular corrugated cardboard tabs. The corrugated cardboard tabs were the same width and thickness of the sides that they were attached to. The tabs each had a first foldline/scoreline, located at the intersection of the top of the section/side and the tab, along which the tab was folded horizontally relative to the top of the section/side to create a ledge and a second foldline/scoreline along which the tab was folded downward relative to the top of the section/side. The distance from the first foldline/scoreline to the second foldline/scoreline was 0.5 inches. The distance from the second foldline/scoreline to the edge of the tab was 1.5 inches. The tabs secured the first water jacket and the expanded polystyrene to the front, rear and sides of the second inner box. A third water jacket consisting of interconnected water cells was placed on the ledge. All of the packaging materials were stabilized at 23° C. for 24 hours.

Figure 12:
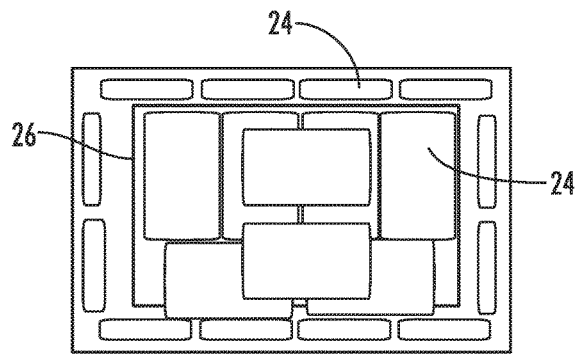
FIG. 12 is a top, plan view of the packout of EXAMPLE 1; the first insulating material and the refrigerant are shown.
Figure 13:
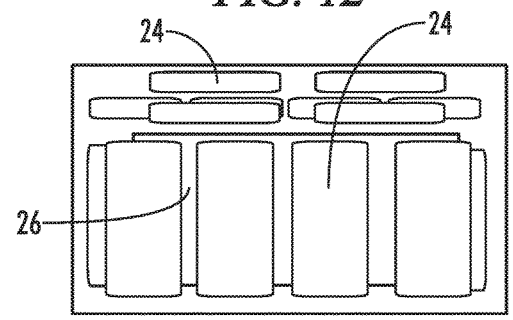
FIG. 13 is a side, elevation view of the packout of EXAMPLE 1; the first insulating material and the refrigerant are shown.
Figure 14:
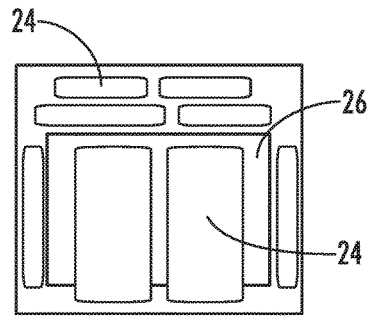
FIG. 14 is a front, elevation view of the packout of EXAMPLE 1; the first insulating material and the refrigerant are shown.

Twenty CGB-1200 (Cryopak, Edison, N.J.) 2 pound frozen gel packs conditioned at −10° C. (+/−2° C.) for 24 hours were provided. Two frozen gel packs were placed between the front of the first inner box and the front wall of the EPS box, two frozen gel packs were placed between the rear of the first inner box and the rear wall of the EPS box, four frozen gel packs were placed between each side of the first inner box and the side walls of the EPS box. Thirty-four eight-ounce plastic water bottles were then placed inside the second inner box. The water inside the plastic water bottles was used to stimulate a payload and the water bottles were stabilized at 4° C. (+/−2° C.) for 48 hours before being loaded into the second inner box. A thermocouple was placed into one of the water bottles. The spaces between the plastic water bottles and the walls of the second inner box were filled with 0.5 inch bubble wrap. The first inner box was taped closed. Six frozen gel packs were placed on top of the first inner box to create a first layer of gel packs and two additional frozen gel packs were placed on the first layer. Top, side, and front views of the packout are shown in FIGS. 12-14, wherein the refrigerants/frozen gel packs are shown as 24 and the first insulating material (i.e., the first inner box) is labeled as 26 consistent with the above numbering scheme.

Two layers of 0.5 inch bubble wrap were placed on top of the top layer of frozen gel packs. The EPS box lid was used to close the top of the EPS box. The top of the ECT-32 corrugated cardboard shipping box was closed and taped shut.

Figure 15:
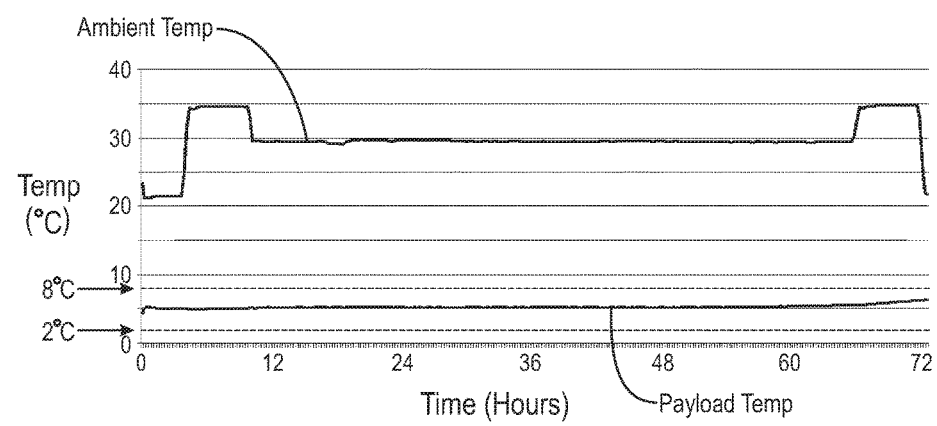
FIG. 15 is a graph showing the temperature of the payload of EXAMPLE 1 over 72 hours.

The ECT-32 corrugated cardboard shipping box was placed into an environmental chamber and subjected to Summer ISTA 7D 72-hour temperature testing (hot shipping and hot receiving) that consisted of 22° C. for four hours, 35° C. for six hours, 30° C. for 56 hours and 35° C. for 6 hours. The results of the test are provided in FIG. 15. As shown in FIG. 15, the temperature inside the water bottle remained between 2-8° C. for the 72 hour testing period.

Example 2

Figure 16:
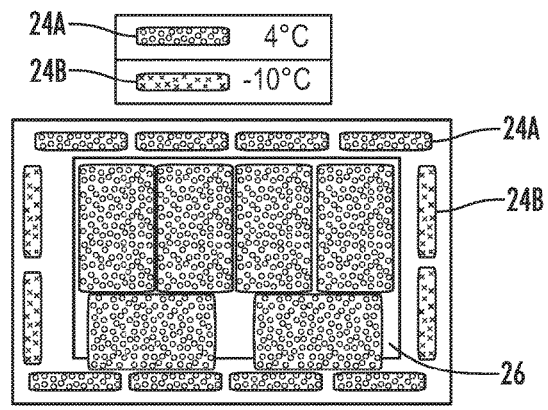
FIG. 16 is a top, plan view of the packout of EXAMPLES 2 and 3; the first insulating material and the refrigerant are shown.
Figure 17:
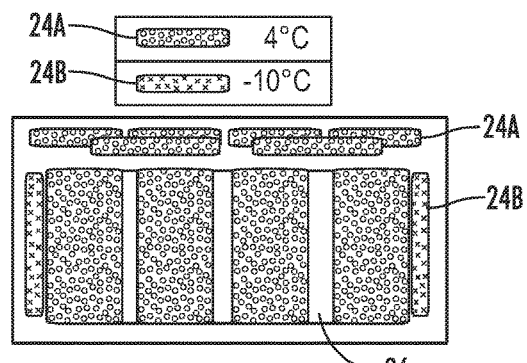
FIG. 17 is a side, elevation view of the packout of EXAMPLES 2 and 3; the first insulating material and the refrigerant are shown.
Figure 18:
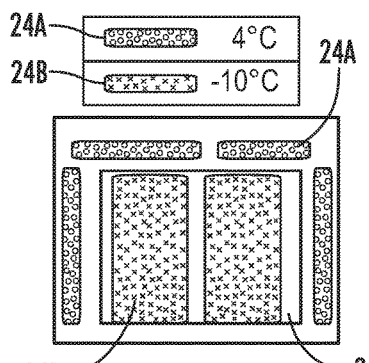
FIG. 18 is a front, elevation view of the packout of EXAMPLES 2 and 3; the first insulating material and the refrigerant are shown.

A temperature controlled shipping box system was prepared as follows. A rectangular ECT-32 (edge crush test) corrugated cardboard shipping box having a front, a rear, two sides, a closed bottom and a closeable top was provided. The shipping box had a length of 26 inches, a width of 17 inches and a height of 16.2 inches and was made of ECT-32 Vs inch thick corrugated cardboard. A rectangular EPS (expanded polystyrene) box having a front, a rear, two sides, a closed bottom, and a top closeable by a lid was placed inside the corrugated cardboard shipping box. The EPS box had a length of 23 inches, a width of 17 inches, a height of 13.2 inches and the expanded polystyrene forming the bottom, sides and lid was 1.5 inches thick and had 3 pcf (pounds per cubic feet) density. A first inner box (i.e., a first insulating material) was placed centrally inside the EPS box. The first inner box was made of 32 ECT inch Vs thick corrugated cardboard, had a front, a rear, two sides, a closed bottom, a closeable top, a length of 20.25 inches, a width of 13.5 inches, and a height of 9 inches. A first water jacket (i.e., a second insulating material) consisting of interconnected water cells and having a thickness of 0.5 inches was placed inside the first inner box and used to line the two sides and front and rear of the inner box. A second water jacket consisting of interconnected water cells and having a thickness of 0.5 inches was placed inside the first inner box and used to line the bottom of the inner box. A second inner ECT-32 corrugated cardboard box (i.e., a third insulating material) having a front, a rear, two sides, a closed bottom, an open top, a thickness of 0.125 inches, a length of 18.75 inches, a width of 11.75 inches, and a height of 7.75 inches was placed interior to the first and second water jackets and used to line the water jackets. The tops of the front, rear and two sides of the second inner corrugated cardboard box were scored to create four rectangular corrugated cardboard tabs. The corrugated cardboard tabs had the same dimensions and foldlines/scorelines as described in EXAMPLE 1. The tabs secured the water jacket to the front, rear and sides of the second inner box. All of the packaging materials were stabilized at 23° C. for 24 hours. Four CGB-1200 (Cryopak, Edison, N.J.) 2 pound frozen gel packs conditioned at −10° C. (+/−2° C.) for 24 hours and fourteen CGB-1200 (Cryopak, Edison, N.J.) 2 pound refrigerated gel packs conditioned at 4° C. (+/−2° C.) for 24 hours were provided. Two frozen gel packs were placed between the front of the first inner box and the front wall of the EPS box and two frozen gel packs were placed between the rear of the first inner box and the rear wall of the EPS box. Four frozen gel packs were placed between each side of the first inner box and the side walls of the EPS box. Five eight ounce bottles of water was then placed inside the second inner box. The water bottles were stabilized at 4° C. (+/−2° C.) for 48 hours before being loaded into the second inner box. A thermocouple was placed into one of the water bottles. The first inner box was taped closed. Six refrigerated gel packs were placed on top of the first inner box. Top, side, and front views of the packout are shown in FIGS. 16-18, wherein the refrigerated gel packs are shown as 24A, the frozen gel packs are shown as 24B and the first insulating material (i.e., the first inner box) is labeled as 26.

1 inch of bubble was placed on top of the top frozen gels. The EPS box lid was used to close the top of the EPS box.

Figure 19:
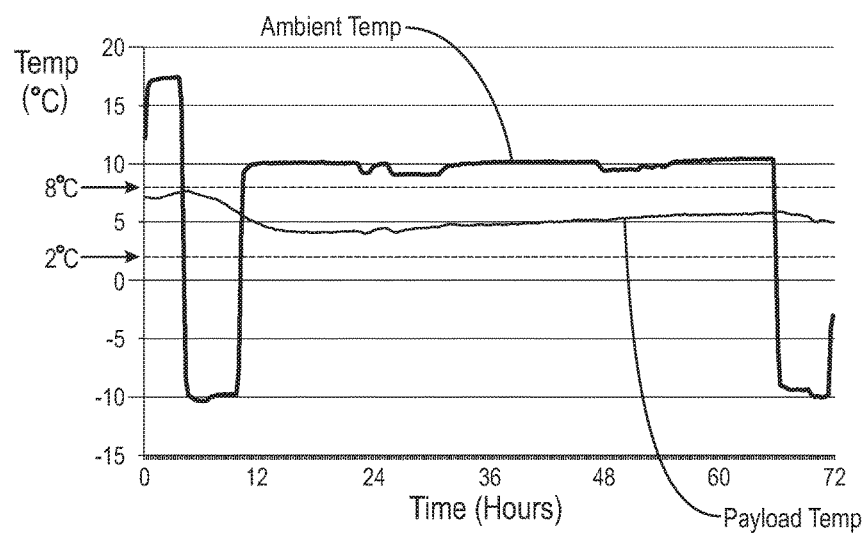
FIG. 19 is a graph showing the temperature of the payload of EXAMPLE 2 over 72 hours.

The ECT-32 corrugated cardboard shipping box was placed into an environmental chamber and subjected to Winter ISTA 7D 72-hour temperature testing that consisted of 18° C. for four hours, −10° C. for six hours, 10° C. for 56 hours and −10° C. for 6 hours. The results of the test are provided in FIG. 19. As shown in FIG. 19, the temperature inside the water bottle remained between 2-8° C. for the 72 hour testing period.

Example 3

Figure 20:
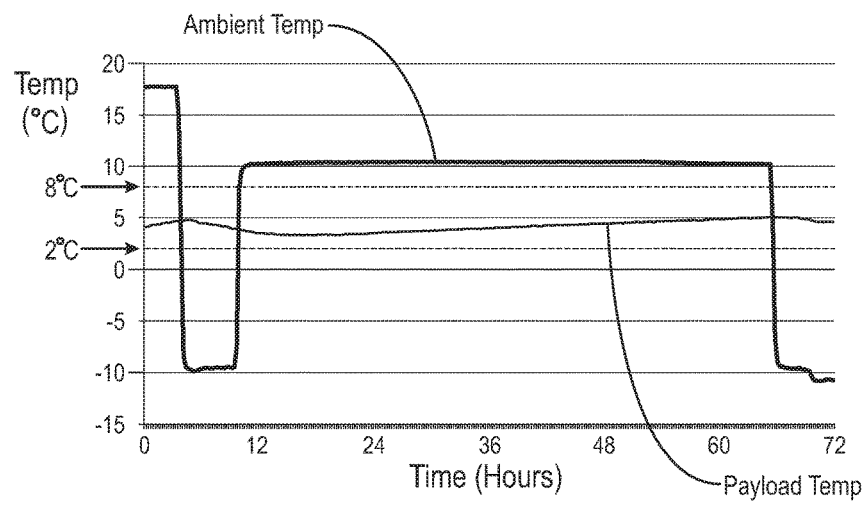
FIG. 20 is a graph showing the temperature of the payload of EXAMPLE 3 over 72 hours.

A third temperature controlled shipping box system identical to EXAMPLE 2 except that the payload was thirty-four eight ounce bottles of water was prepared and subjected to Winter ISTA 7D 72-hour temperature testing as described in EXAMPLE 2 directly above. As shown in FIG. 20, the temperature inside the water bottle remained between 2-8° C. for the 72 hour testing period.

Example 4

A temperature controlled shipping box system was prepared as follows. A rectangular ECT-32 (edge crush test) corrugated cardboard shipping box having a front, a rear, two sides, a closed bottom and a closeable top was provided. The shipping box had a length of 26 inches, a width of 17 inches and a height of 16.2 inches and was made of ECT-32⅛ inch thick corrugated cardboard. A rectangular EPS (expanded polystyrene) box having a front, a rear, two sides, a closed bottom, and a top closeable by a lid was placed inside the corrugated cardboard shipping box. The EPS box had a length of 23.5 inches, a width of 16.5 inches, a height of 14.5 inches and the expanded polystyrene forming the bottom, front, rear, two sides and lid was 2 inches thick and had 1.35-1.5 pcf (pounds per cubic feet) density.

Four CGB-1200 (Cryopak, Edison, N.J.) 2 pound frozen gel packs conditioned at −10° C. (+/−2° C.) for over 48 hours were placed at the bottom of the EPS box.

A rectangular inner box with a bottom, a front, a rear, two sides and a top closeable by a lid was placed centrally inside the EPS box. Excluding the size of the lid, the inner box was 18.25 inches in length, 11.5 inches in width and 6.625 inches in height. The sides, front, and rear of the box consisted of an outer panel of 0.125 inch thick 32 ECT corrugated cardboard (B Flute), a middle panel of 0.25 inch blue board (extruded polystyrene), and an inner panel of 0.125 inch thick 32 ECT corrugated cardboard (B Flute). The outer, middle and inner panels spanned the entire the width and length of the front, rear and sides, respectively. The bottom of the box (from top to bottom) consisted of a 17.5 inch long by 10.75 inch in width top panel of 0.125 inch thick 32 ECT corrugated cardboard (B Flute), a first middle panel consisting of 12.5 inch long by 6.5 inch in width by 0.25 inches thick water jacket taped to the bottom of the top panel (the water jacket was centrally located with respect to the length and width of the top panel), a second middle panel consisting of 17 inch long by 8.875 inch wide by 0.125 inch thick 32 ECT corrugated cardboard (B Flute), a third middle panel consisting of 17.5 inch long by 10.625 inch wide by 0.125 inch thick 32 ECT corrugated cardboard (B Flute), a fourth middle panel consisting of 17.875 inch long by 11.5 inch wide by 0.875 inch thick polyurethane, and a bottom panel consisting of four pieces of 0.125 inch thick 32 ECT corrugated cardboard that met to form a 18 inch long by 11.5 inches wide bottom panel. In addition, as noted above, the water jacket was only 12.5 inches long by 6.5 inches wide whereas the top panel was 17.5 inches long by 10.75 inches wide so that the water jacket covered only about 43.2% of the surface area of the bottom of the top panel. A payload consisting of 28 eight-ounce water bottles was loaded into the inner box. The water bottles were positioned vertically in the inner box (and not stacked on top of each other) so that there were 4 rows and 7 columns of water bottles. Thermocouples were positioned inside one of the center water bottles and inside the water bottles in the upper right and lower left hand corners of the inner box. (Because there were four rows and seven columns of water bottles, the box had two center water bottles. One of these center bottles was chosen for temperature measurement).

A rectangular lid was placed on the inner box. The lid was 19 inches long by 12 inches wide by 3.25 inches in height. The lid had a front, a rear, two sides an open bottom, and a top. The two sides consisted of 19 inch long by 3.25 inches high by 0.125 inch thick 32 ECT corrugated cardboard (B Flute). The front and back consisted of 12 inch long by 3.25 inches high by 0.125 inch thick 32 ECT corrugated cardboard (B Flute). The lid top was 19 inches long by 12 inches wide and consisted of a bottom panel of two 0.125 inch thick 32 ECT corrugated cardboard (B Flute) panels that met to form a 18.5 inch long by 11.625 inch wide bottom panel, a middle panel consisting of 12 inch long by 5.75 inches wide by 0.25 inch thick water jacket, and a top panel consisting of 19 inches long by 12 inches wide by 0.125 inches thick 32 ECT (B Flute) corrugated cardboard. The water jacket was taped to the bottom of the top panel, was centrally located with respect to the top panel, and covered only about 28.9% of the surface area of the bottom of the top panel.

Four CGB-1200 (Cryopak, Edison, N.J.) 2 pound frozen gel packs conditioned at −10° C. (+/−2° C.) for over 48 hours were placed on top of the inner box lid. An additional four CGB-1200 (Cryopak, Edison, N.J.) 2 pound frozen gel packs conditioned at −10° C. (+/−2° C.) for over 48 hours were placed on top of these four gel packs. FIG. 32 is a side, perspective exploded view showing the packout. (Only one water bottle is shown for purposes of clarity).

Two identical shipping boxes were packed as described directly above so that three shipping boxes in total were packed. Except for the gel packs and payload, none of the box components was pre-conditioned and instead the components were provided at room temperature.

Figure 31:
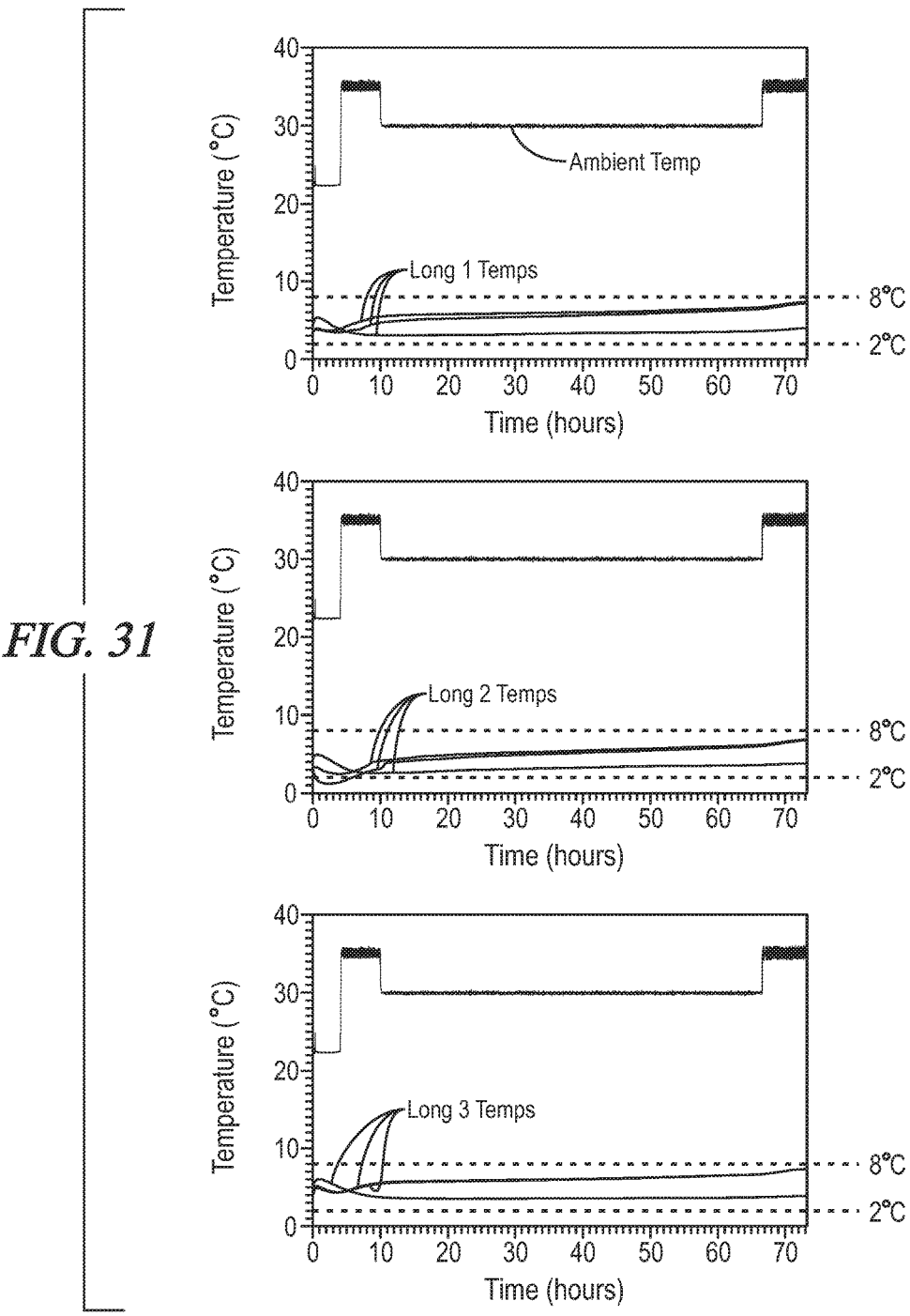
FIG. 31 are graphs showing the temperature of the payloads of the three box systems of EXAMPLE 4 over 72 hours.

The three ECT-32 corrugated cardboard shipping boxes were placed into an environmental chamber and subjected to Summer ISTA 7D 72-hour (2007) temperature testing (hot shipping and hot receiving) that consisted of 22° C. for four hours, 35° C. for six hours, 30° C. for 56 hours and 35° C. for 6 hours. The three boxes were internally designated as Long 1, Long 2 and Long 3, respectively. The results of the test are provided in FIG. 31. As shown in FIG. 31, each box (Long 1, Long 2 and Long 3) had three thermocouple readings—one in the center water bottle, one in the upper right water bottle, and one in the lower left water bottle. As shown in FIG. 31, the temperature inside all water bottles remained between 2-8° C. for the 72 hour testing period, except for a single Long 2 water bottle, whose temperature dropped below 2° C. for a brief period. The reason for this variance was attributed to the fact that the thermocouple for this water bottle was positioned near the top of the water bottle. In the opinion of the experiment conductor, all three boxes passed—i.e., maintained the payload at 2-8° C. for the 72 hour testing period under ISTA 7D (Summer)(2007). It was also predicted that the three boxes would pass ISTA 7D (Winter)(2007) and ISTA 7E (Summer and Winter)(2010) because it is easier to maintain the payload at 2-8° C. for 72 hours under these three other testing conditions.

Comparative Example 1

A control box was prepared identical to the system of EXAMPLE 1 above except that the control box did not contain a water jacket (i.e., a second insulating material) or rectangular strips of 3 pound expanded polystyrene (i.e., a third insulating material) and the control box only contained five water bottles. To mimic the thickness of the water jacket and expanded polystyrene strips along the two sides and front and rear, corrugated cardboard was placed between the two sides and front and rear of the first and second inner boxes.

Figure 21:
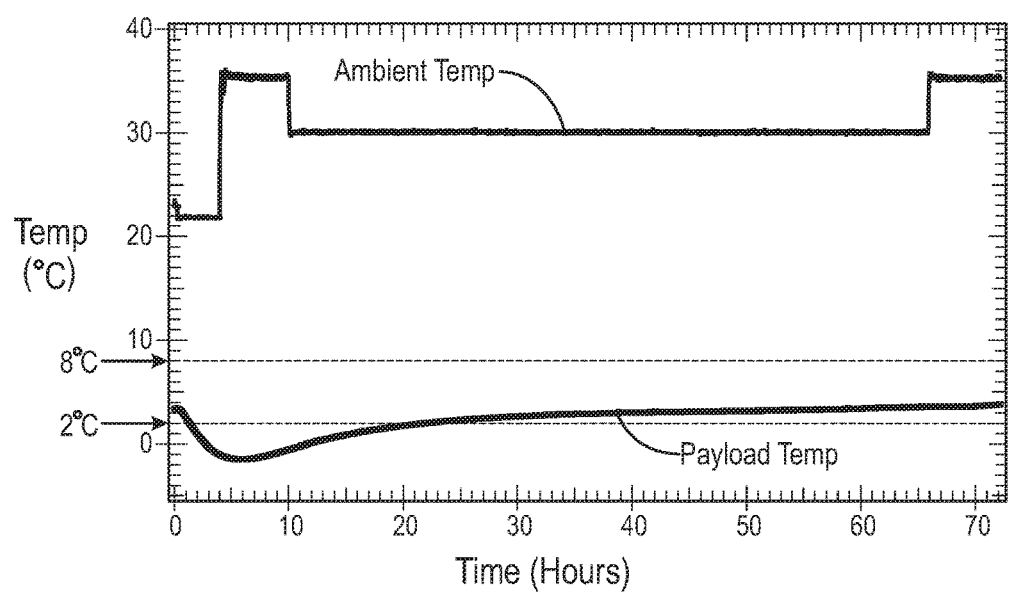
FIG. 21 is a graph showing the temperature of the payload of COMPARATIVE EXAMPLE 1 over 72 hours.

The ECT-32 corrugated cardboard shipping box of COMPARATIVE EXAMPLE 1 was placed into an environmental chamber and subjected to Summer ISTA 7D 72-hour temperature testing (hot shipping and hot receiving) that consisted of 22° C. for four hours, 35° C. for six hours, 30° C. for 56 hours and 35° C. for 6 hours. The initial temperature reading of the thermocouple inside the water bottle was 3.2° C. Less than 2 hours into the testing, the temperature inside the water bottle dropped to 1.7° C. and 3 hours into the testing, the temperature inside the water bottle dropped to 0.3° C. The results of the test are provided in FIG. 21.

The following conclusions can be drawn from EXAMPLE 1 and COMPARATIVE EXAMPLE 1: Without the insulant system of the present disclosure, the payload will be subject to cold shock by ice packs.

What is claimed is:

1. A container system comprising:
a) a first outer container having an exterior and an interior;
b) a refrigerant disposed in said first outer container interior;
c) a payload container comprising an interior and an exterior, said payload container disposed interior to said refrigerant within said first outer container interior;
d) a payload disposed in said payload container interior;
e) a first insulating material disposed between said refrigerant and said payload container, wherein said first insulating material is cardboard;
f) a second insulating material disposed between said first insulating material and said payload container, wherein said second insulating material is a container comprising liquid water; and
g) a third insulating material disposed between said second insulating material and said payload container, wherein said third insulating material is cardboard.

2. The container system of claim 1, wherein the system further comprises a fourth insulating material disposed between said first insulating material and said third insulating material, wherein said fourth insulating material is an insulating material other than cardboard.

3. The container system of claim 1 wherein said refrigerant is a frozen water-based refrigerant, wherein said second insulating material is at room temperature, and further wherein said payload is a medicine having a temperature between 2 and 8 degrees Celsius.

4. The container system of claim 1 wherein said payload is a medicine.

5. The container system of claim 4 wherein said container system is configured to maintain said medicine at a temperature of between 2 degrees and 8 degrees Celsius for at least 72 hours when the container system is subjected to 22 degrees Celsius for the first four hours, 35 degrees Celsius for the next six hours, 30 degrees Celsius for the next 56 hours and 35 degrees Celsius for the last six hours.

6. The container system of claim 5 wherein said refrigerant comprises a plurality of frozen gel packs having the same temperature.

7. The container system of claim 6 wherein said first outer container interior contains no more than 0.25 pounds of a phase change material having a melting point between 2 degrees Celsius and 8 degrees Celsius.

8. The container system of claim 1 wherein said first insulating material forms at least a portion of a first insulating layer, wherein said second insulating material forms at least a portion of a second insulating layer, wherein said third insulating material forms at least a portion of a third insulating layer, and further wherein said second insulating layer is between said first insulating layer and said third insulating layer.

9. The container system of claim 1 wherein said container system further comprises a second outer container, said second outer container comprised of cardboard and comprising a second outer container interior, wherein said first outer container is comprised of an insulating material other than cardboard, and further wherein said first outer container is located in the second outer container interior.

* * * * *